United States Patent [19]

Solomon et al.

[11] Patent Number: 4,652,755
[45] Date of Patent: Mar. 24, 1987

[54] METHOD AND APPARATUS FOR ANALYZING PARTICLE-CONTAINING GASEOUS SUSPENSIONS

[75] Inventors: Peter R. Solomon, West Hartford; Robert M. Carangelo, Coventry; Philip E. Best, Mansfield, all of Conn.

[73] Assignee: Advanced Fuel Research, Inc., East Hartford, Conn.

[21] Appl. No.: 690,301

[22] Filed: Jan. 10, 1985

[51] Int. Cl.[4] ................ G01N 21/37; G01N 21/51; G01N 21/59

[52] U.S. Cl. .................................. 250/341; 250/338; 250/343; 250/345; 250/347; 250/349; 250/352; 250/339; 356/346; 356/439; 356/441; 356/442

[58] Field of Search ................ 250/338 GA, 339, 341, 250/343, 344, 345, 373, 347, 349, 352, 574; 356/441, 342, 346, 439, 442

[56] References Cited

U.S. PATENT DOCUMENTS

| | | | |
|---|---|---|---|
| 2,333,762 | 11/1943 | Bertrand | 356/312 |
| 2,844,032 | 7/1958 | Tandler et al. | 374/123 |
| 2,878,388 | 3/1959 | Bergson | 250/373 |
| 3,317,730 | 5/1967 | Hilsum | 250/338 |
| 3,478,206 | 11/1969 | Gaglione | 250/428 |
| 3,588,496 | 6/1971 | Snowman | 250/343 |
| 3,631,237 | 12/1971 | Sole | 250/395 |
| 3,700,333 | 10/1972 | Charlson et al. | 356/339 |
| 3,703,337 | 11/1972 | Neugroschel et al. | 356/407 |
| 3,724,951 | 4/1973 | Seelbinder | 356/336 |
| 3,730,630 | 5/1973 | Witte | 356/312 |
| 3,743,430 | 7/1973 | Riggs | 356/435 |
| 3,787,122 | 1/1974 | Lepper, Jr. | 356/338 |
| 3,882,477 | 5/1975 | Mueller | 340/510 |
| 3,924,469 | 12/1975 | Brandli et al. | 374/129 |
| 3,977,787 | 8/1976 | Fletcher et al. | 356/346 |
| 4,014,612 | 3/1977 | Atwood et al. | 356/325 |
| 4,017,193 | 4/1977 | Loiterman | 356/435 |
| 4,021,713 | 5/1977 | Suga | 250/574 |
| 4,095,899 | 6/1978 | Vanasse | 356/346 |
| 4,142,417 | 3/1979 | Cashdollar et al. | 374/110 |
| 4,264,206 | 4/1981 | Hattori | 356/343 |
| 4,304,491 | 12/1981 | Kraushaar et al. | 356/326 |
| 4,440,510 | 4/1984 | Stein | 374/169 |
| 4,448,887 | 5/1984 | Kauffman et al. | 436/60 |
| 4,453,226 | 6/1984 | Hobbs et al. | 364/555 |
| 4,492,467 | 1/1985 | Drain et al. | 356/336 |
| 4,501,968 | 2/1985 | Ebi et al. | 250/343 |
| 4,507,556 | 3/1985 | Brenholdt | 250/341 |

OTHER PUBLICATIONS

Gumbrecht, R. O. and Sliepscevich, C. M., "Scattering of Light by Large Spherical Particles" *J. Phys. Chem.* 57, pp. 90–95 (1953).

Buckius, R. O. and Tien, C. L., "Infrared Flame Radiation" *Int. J. Heat Mass Transfer*, vol. 20, pp. 93–106 (1977).

Coppalle, A. and Vervisch, P., "The Total Emissivities of High-Temperature Flames" *Combustion and Flame*, vol. 49, pp. 101–108 (1983).

D'Alessio, A., Cavaliere, A., and Menna, P., "Theoretical Models for the Interpretation of Light Scattering by Particles Present in Combustion Systems" *Soot in Combustion Systems*, Edited by J. Lahaye and G. Prado, vol. 7, pp. 327–353, (Plenumn Press, NY), (1983).

Coppalle, A. and Vervisch, P., "Fire Flame Radiation" *Combustion and Flame*, vol. 52, pp. 127–135 (1983).

Best, P. E., Carangelo, R. M. and Solomon, P. R., "FT-IR Determination of Coal and Soot Particle Temperatures During Pyrolysis", ACS Div. of Fuel Chemistry Preprints, vol. 29 (1984).

*Primary Examiner*—Janice A. Howell
*Assistant Examiner*—Constantine Hannaher

[57] ABSTRACT

The method and apparatus permit analyses, by optical means, of properties of gaseous suspensions of particles, by measuring radiation that is emitted, transmitted or scattered by the particles. Determinations of composition, size, temperature and spectral emittance can be performed either in-situ or by sampling, and Fourier-transform infrared spectrometric techniques are most effectively used. Apparatus specifically adapted for performing radiation scattering analyses, and for collecting radiation from different sources, are provided.

59 Claims, 51 Drawing Figures

KCl
95 micrometer diameter

Ash
~10 micron diameter

Lignite
60 micron diameter

JP-7 Droplets
180 micron diameter

METHOD AND APPARATUS FOR ANALYZING PARTICLE-CONTAINING GASEOUS SUSPENSIONS

The Government has rights in this invention pursuant to Contract No. DE-AC21-81FE05122 awarded by the U.S. Department of Energy.

BACKGROUND OF THE INVENTION

Many processes require, or would at least benefit from, on-line monitoring of the chemical composition and/or other parameters of gaseous suspensions involved. Such in-situ analysis entails a number of significant advantages over other techniques (e.g., the analysis of conversion products), particularly in that all of the problems associated with sampling and sample handling are inherently eliminated; it also permits dynamic monitoring of chemical and/or physical changes that occur during the course of combustion, pyrolysis, and other types of reactions.

As far as is known, very few (if any) of the forms of instrumentation heretofore available are useful or satisfactory for the on-line analysis of particle streams (as used herein, reference to "particles" is to be understood to include liquids and solids, as well as mixed phases). In particular, it is not believed that any such instrumentation is capable of resolving size, temperature, number density and/or quantitative chemical composition for particle-containing gaseous streams, especially in a reactive environment.

It is of course well known to utilize electromagnetic radiation for a variety of analytical purposes, as evidenced by the body of prior art patents issued in the United States. For example, in Bertrand U.S. Pat. No. 2,333,762 an analytical technique is disclosed in which the intensity of radiation is used to determine the solid content of a gaseous medium. A temperature measurement system, operating upon absorbed and emitted radiation, is described in Tandler et al Pat. No. 2,844,032, and in Pat. No. 2,878,388 Bergson discloses a system for analyzing gases by measuring the absorption of radiant energy.

Seelbinder Pat. No. 3,724,951 and Riggs Pat. No. 3,743,430 both involve techniques for making aerosol opacity determinations, based upon transmitted radiation, and Snowman Pat. No. 3,588,496 teaches radiation absorption analysis apparatus for identifying samples of gases, aerosols and liquids. Each of the following patents uses irradiation scattering as a basis for detecting and/or analyzing aerosols or smokes: Hilsum Pat. No. 3,317,730, Charlson et al Pat. No. 3,700,333, Lepper, Jr. Pat. No. 3,787,122, and Mueller Pat. No. 3,882,477. In Patent No. 4,017,193, Loiterman describes apparatus for measuring the transmittance of a gaseous medium carrying particulate matter through a conduit, and Suga Pat. No. 4,021,713 discloses apparatus for the sequential measurement of radiation transmitted through smoke.

Neugroschel Pat. No. 3,703,337 discloses an analytical processor capable of handling at least two characteristics of the specimen, simultaneously measuring and converting them for digital print out. Vanesse Pat. No. 4,095,899 concerns a technique for performing Fourier spectroscopy. In Cashdollar et al Pat. No. 4,142,417, an infrared pyrometer is used to determine radiation emitted from a gas and/or particle, with temperatures being determined by correlation of the radiation data to black-body radiation curves. Kraushaar et al Pat. No. 4,304,491 discloses the use of a spectrometer to detect both dispersed and undispersed irradiation for IR imaging.

Cells and associated devices, used for spectroscopic analysis of samples, are described in Gaglione Pat. No. 3,478,206, Sole et al Pat. No. 3,631,237 and Witte Pat. No. 3,730,630. Surface temperature measuring apparatus is taught by Brandli et al in Pat. No. 3,924,469, and a photometer/detector/amplifier arrangement, for use in automatic analysis apparatus, is shown in Atwood et al Pat. No. 4,014,612.

In Stein Pat. No. 4,440,510, a system is disclosed for pyrometric gas temperature measurement, carried out by adjusting and comparing the physical temperature of a black-body with the radiation temperature thereof measured through the gas. A spectrometric method for determining the size of metal particles in oils is taught in Kauffman et al Pat. No. 4,448,887, and a method and apparatus for determining size distribution of particles, by fitting a selected parameter distribution function to scaler representations of data obtained, is disclosed in Hobbs et al Pat. No. 4,453,226.

Finally, in an article entitled "Fire Flame Radiation" (*Combustion and Flame* 52: 127–135, 1983), Vervisch and Coppalle discuss the use of normalized emission measurements for determining the temperature of flames containing soot.

Despite the foregoing, a need remains for means by which analyses of the sort described above can be carried out conveniently and effectively.

Accordingly, it is a primary object of the present invention to provide a novel method and apparatus by which gaseous suspensions of liquid and/or solid particles can readily be analyzed for any of a variety of physical and chemical properties.

More specific objects are to provide such a method and apparatus by which such a suspension can be analyzed either in-situ, in a reactive environment, or as a supplied sample, for determinations of particle size, temperature, number density, spectral emittance, and/or composition, in a manner that is very fast, convenient, and effective.

SUMMARY OF THE INVENTION

It has now been found that certain of the foregoing and related objects of the invention are readily attained by the provision of apparatus comprising, in combination, interferometer means, radiation collecting means, radiation source means, and electronic data processing means for analyzing collected radiation. The interferometer means is operatively positionable, with respect to the suspension to be analyzed, for encoding radiation projected thereinto and emanating therefrom, and the collecting means is similarly positionable, with respect to the suspension and the interferometer means, for collecting coded radiation from the suspension; the collecting means is also adapted to discriminate, in cooperation with the data processing means, radiation transmitted through the suspension from radiation emanating therefrom. An electromagnetic radiation beam is provided by the source means, so as to be projected through the interferometer means for coding and thereafter for transmission through the suspension.

It should be noted that, as used herein, reference to radiation "emanating" from the suspension or containment means is intended to be exclusive of radiation which is transmitted by or through the suspension or the particles thereof, but inclusive of any radiation that is emitted by the particle and/or scattered by interaction therewith. Also, "transmitted" radiation is that which passes directly through the substance, without being diverted (such as by refraction, diffraction or scattering by another mechanism) from its original rectilinear path.

In preferred embodiments of the apparatus, the collecting means will comprise a first collector operatively positionable for collecting radiation transmitted through the suspension, and a second collector separate from the first, operatively positionable for collecting the radiation emanating from the suspension. Generally, the apparatus will be adapted for use with containment means having a sidewall defining a chamber for the gaseous suspension. The sidewall of the containment means will in turn have at least one port providing optical access into the chamber, with the "second" collector, and the source means and/or the "first" collector, being disposed on the apparatus for positioning so as to function through the port.

In most instances, however, the apparatus will be adapted for use with containment means having a pair of optical access ports aligned transversely on opposite sides of its sidewall. The source means and "first" collector of such apparatus will be in effective optical alignment, and spaced from one another to accommodate the containment means therebetween, thereby permitting projection of the beam from the source means through the aligned access ports to the "first" collector. The apparatus will desirably include means defining an aperture of variable size, from which passes the transmitted radiation for collection by the "first" collector; this will enhance the usefulness of the apparatus for making particle size determinations.

For some applications, the apparatus will additionally include a cell, cooperatively providing the above-described containment means as an integral component of the apparatus, together with associated means for injection of the gaseous suspension. In a specific embodiment, the cell has a generally cylindrical sidewall and end walls cooperatively defining the chamber thereof. The sidewall has a pair of optical access ports positioned diametrically thereon, and the end walls have means defining inlet and outlet channels therethrough, which channels are aligned substantially on the longitudinal axis of the cell for the injection and removal of particles, respectively. Such a cell will also have means by which the temperature of the inside surface of the sidewall, and the temperature of the inlet and outlet channel-defining means, can be independently controlled.

In other preferred embodiments of the apparatus, the "second" collector will be effectively disposed along the path of radiation between the source means and the interferometer, and the apparatus will additionally include diverter means for establishing a radiation path between the gaseous suspension and either the source means, the "second" collector, or both. The diverter means may be operative to either permit passage of radiation from the source means to the suspension, or to block such passage of radiation while simultaneously directing radiation from the suspension to the "second" collecting means. As a result, measurements of radiation transmitted through and emanating from the suspension, respectively, can be selectively made.

Most desirably, the diverter means will be adapted to simultaneously permit passage of radiation from the source means to the suspension while also directing radiation therefrom to the "second" collecting means. To do so, the diverter means may have a first portion which is transparent to the radiation from the source means, and a second portion which is opaque thereto and is reflective of radiation emanating from the suspension, and is directed theretoward. Thus, the diverter means will permit the transmitted and emanating radiation to be simultaneously measured, using the "first" and "second" collecting means, respectively.

In the particularly preferred embodiments, the apparatus will comprise a Fourier-transform spectrometer, adapted to develop a spectrum representative of the intensity of the collected radiation as a function of wavenumber. For that purpose, the data processing means of the spectrometer will be programmed to compare the representative spectrum to preestablished spectra indicative of a parameter for which the gaseous suspension is being analyzed, so as to fit the representative spectrum thereto and thereby determine the parameter. More specifically, the spectrometer will employ radiation source means operating in the infrared wavelengths regions, and the data processing means will beneficially be programmed to effect the comparisons involved by application of at least one of the following generalized formulas:

$$E = \frac{[k_s BB(T_s) + k_g BB(T_g) + NA\epsilon BB(T_p) + NAQ_s BB(T_w)][1 - \exp(-(k_s + k_g + NAQ_{ext})L)]}{k_s + k_g + NAQ_{ext}}$$

and $$(1-\tau) = 1 - \exp[-(k_s + k_g + NAQ_{ext})L].$$

As used therein (and in other expressions throughout this specification), "E" represents any collected radiation emanating from the gaseous suspension and not transmitted therethrough; "$\tau$" represents the ratio of any collected radiation that is transmitted through the suspension, divided by radiation that would be transmitted in the absence thereof (i.e., transmittance); "$k_s$" and "$k_g$" are the extinction coefficients for any soot present and the gas phases, respectively, of the suspension; "$BB(T_s)$", "$BB(T_g)$", "$BB(T_p)$", and "$BB(T_w)$" are the black-body spectra appropriate to the temperature of any soot present, the gas, the particles, and the medium surrounding the suspension, respectively; "N" is the number density of the particles in the suspension; "A" is the geometric cross-sectional area of the particles; "L" is the effective path length through the gaseous suspension; "$\epsilon$" is the spectral emittance of the particles; "$Q_s$" is the ratio of the radiation scattering cross section to the geometric cross section of the particles; and "$Q_{ext}$" is the ratio of the extinction cross section to the geometric cross section of the particles, and is equal to $Q_s + Q_{abs}$. The term "$Q_{abs}$" is used to represent the ratio of the absorption cross section to the geometric cross section of the particles, and it should be appreciated that each of the foregoing quantities, other than N, A and L, is wavenumber dependent.

The foregoing generalized formula for "E" is a special case of a more basic equation, in which special case the sample is homogeneous and all quantities are therefore independent of position through the sample volume. The data processing means of the apparatus may, however, be programmed to effect comparison of the representative spectrum using the following basic equation, by which contributions from theoretical slices of width "dl", at positions "1" through the suspension, are integrated for values of "1" from zero to "L" to determine the radiation emanating from a non-homogeneous sample:

$$E = \int_0^L [\{k_s BB(T_s) + k_g BB(T_g) + NA\epsilon BB(T_p) + NAQ_s BB(T_w)\} \exp(-y)] dl,$$

wherein "y" is the integral:

$$\int_0^1 (k_g + k_s + NAQ_{ext}) dl'.$$

It will be appreciated that equations other than the foregoing generalized formula for E may also be derived from the basic equation, and used in the apparatus and method of the invention, for other special cases in which particular conditions may exist or be assumed to exist as a practical matter, as will be discussed more fully hereinbelow.

Other objects of the invention are attained by the provision of apparatus particularly adapted for the analysis of a gaseous suspension to determine compositional parameters of the particles contained therein, utilizing refracted components of radiation. Such apparatus will comprise containment means having a sidewall defining a chamber for the flow of a gaseous suspension of particles along a path therethrough, with at least one port being provided in the sidewall to afford optical access to the path. Source means used for providing electromagnetic radiation in the apparatus will be adapted to direct the radiation inwardly from substantially all peripheral points about the path, and the apparatus will have means for collecting radiation emanating from the containment means. To enable the compositional analysis to be made, the containment means, the source means, and the collecting means will be so adapted that components of radiation from the source means that have been refracted or otherwise diverted from their original paths, due to interaction with the particles of the suspension, can be substantially discriminated from radiation that has not been so diverted. Preferably, such apparatus will additionally include second source means, for providing an electromagnetic radiation beam, and second radiation collecting means, the second source means and second collecting means being disposed in effective optical alignment with one another, and being adapted to measure radiation transmitted by the particles of the suspension during passage through the containment means. Generally, the apparatus will also include electronic data processing means for analyzing the radiation collected by the "first" and "second" collecting means, and for also controlling operation of the "second" source means.

In particularly preferred embodiments of the apparatus, the sidewall of the containment means will substantially surround the flow path, and will have an energy radiating surface thereon to provide the first-mentioned source means, which surface will usually be heated for that purpose. The configuration of the wall surface, and the positions thereof and of the collecting means with respect to the access port(s), will substantially limit the radiation from the radiating surface impinging upon the collecting means to that which has been so diverted, thereby effectively providing the radiation discrimination capability of the apparatus. Most desirably, the radiating surface will be of generally circular cross-sectional configuration in planes transverse to the flow path axis, and the sidewall defining it will have a second optical access port therein aligned transversely with the "one" port on the opposite side of the flow path. The "second" port will provide a non-radiating area on the surface, and thereby cooperate to provide the discrimination capability of the apparatus. An interferometer or other coding means, radiation diverter means, and other specific features described above may also be incorporated into the apparatus of this embodiment.

Additional objects of the invention are attained by the provisions of analytical methods, broadly defined to comprise the steps of: a. causing electromagnetic radiation from at least one source to impinge upon a gaseous suspension of liquid and/or solid particles to be analyzed; b. collecting spectral radiation from the so-irradiated suspension; c. developing a spectrum representative of the intensity of the collected radiation as a function of wavenumber; and d. comparing the representative spectrum to preestablished spectra indicative of the parameter for which the suspension is being analyzed, and fitting the representative spectrum thereto to determine the parameter, the comparison being made by application of the equations and formulas set forth and defined herein.

In some cases, the method will include the step of passing the gaseous suspension through a chamber at a flow rate of about 1 to 100 meters per second, with the suspension being irradiated during such passage, and a stream of gas may be passed into the chamber simultaneously with, and as a sheath about, the particle suspension. Normally, the irradiation used will be a beam of infrared wavelengths, preferably brought to a focal volume or zone within the chamber with the gaseous suspension being passed substantially therethrough the focal volume. For certain purposes, it will be advantageous for the particles of the suspension to be in the form of a monodispersed stream, and in the most preferred embodiments of the method the step of analyzing the radiation will comprise Fourier-transform spectroscopic measurement thereof.

In more specific aspects of the method, radiation transmitted through the irradiated suspension, as measured by transmittance $\tau$, is discriminated from radiation "E" emanating therefrom, with spectra representative of the intensity of the radiation $\tau$ and E so collected and discriminated being developed as functions of wavenumber. Preferably, the comparison of the representative and preestablished spectra, for determining the desired parameter, will be made by application of the generalized formulas given above, or by application of the basic equation referred to, or other equations derived therefrom, depending upon the nature of the sample.

In the method, the particles of the suspension may be at a temperature "$T_p$" which is to be determined, the representative spectrum used for comparison being that of normalized emission "$E_n$", wherein $E_n = E/(1-\tau)$. When irradiation is carried out with the gaseous suspension contained in a chamber, the surrounding medium will be the wall surface defining the chamber, and the comparison of spectra will be made based upon the following equation, derived on the basis that $Q_{ext}$ equals 1, and $k_s$ and $k_g$ both equal zero: $E_n = \epsilon BB(T_p) + (1-\epsilon) BB(T_w)$.

In other instances, the temperature of the particles and the temperature of the medium surrounding the suspension will be known, and the parameter for analysis will be emittance "$\epsilon$", the representative spectrum used again being normalized emission. If particle temperature "$T_p$" is substantially higher than the surrounding medium temperature "$T_w$", the comparison will be made based upon the equation: $\epsilon = E_n/BB(T_p)$. If, on the other hand, the surrounding medium comprises the surface of a wall, the temperature of which is substantially higher than that of the particle, the comparison will be made based upon the equation: $\epsilon = 1 - [E_n/BB(T_w)]$. In the latter instance, the method may include the further step of estimating the wavenumber-dependent linear absorption coefficient characteristic "$k_\alpha$" of the composition. This may be done by measuring the value of $E_n$, determining a value for the average transmission "$T'$" for the inside of the particles of the suspension by application of the equation: $T' = E_n/BB(T_w)$, characterizing the gross geometry of the particles of the suspension, in terms of a characterizing dimension "D", selecting a suitable preestablished curve expressing $(-\ln T')$ as a function of $k_\alpha D$, based upon that characterization, and estimating the value of $k_\alpha$ from the selected curve.

In an embodiment of the method that is specifically adapted for quantitative compositional analysis, electromagnetic radiation will be caused to impinge at off-axis angles upon the particles of the suspension during passage through a chamber, such angles consisting essentially of angles that are oblique to the optical access port thereof. The collected radiation is substantially limited, by virtue of the off-axis impingement, to rays coming from the source that are refracted or otherwise diverted by the particles. A spectrum representative of the path and amplitude of the collected radiation is developed, as a function of wavenumber, and is compared and fitted to preestablished spectra indicative of the compositional parameter for which the suspension is being analyzed, to determine the same.

Generally, the cavity used in performing such a method will be defined by a wall substantially surrounding the gaseous suspension, the surface of which will be maintained at a temperature substantially higher than the temperature of the particles, thereby providing an off-axis, infrared radiation source. Typically, the wall surface will be at a temperature that is about 500 kelvin or more above that of the particles, and the suspension will desirably be maintained, prior to entry into the cavity, at a temperature suitable to ensure that they will be substantially at room temperature therewithin; the flow rate of the suspension through the chamber should be sufficiently high to avoid substantial heating of the particles by the radiant energy. As an alternative to using a hot surrounding wall surface, a high intensity radiation source (such as laser beam optics) may be moved to incrementally displaced circumferential positions about the path of the suspension, to provide an off-axis beam at a multiplicity of angular relationships.

In especially preferred embodiments of the method for compositional analysis, a beam of electromagnetic radiation from a second source will also be caused to impinge upon the particles, with the collecting step being carried out by collecting and discriminating the diverted rays from the components of the second-source beam that are transmitted through the particles. The representative spectrum used for comparison will again be that of normalized emission, with the comparison being made by application of the designated formulae or equations. In such a case, the transmitted radiation components and the diverted rays may be collected sequentially, under conditions of constant particle flow rate and density, or they may preferably be collected simultaneously. This embodiment of the method may also include the further step of estimating the wavenumber-dependent linear absorbtion coefficient characteristic "$k_\alpha$" of the composition, in the manner described above.

Finally, the method may be employed for the analysis of the size of particles in a gaseous suspension, by causing a beam of electromagnetic radiation to impinge upon the suspension, and selectively collecting radiation transmitted therethrough. A spectrum representative of the intensity of the collected radiation, as a function of wavenumber, is developed, and is compared and fitted to preestablished spectra indicative of particle size. The representative spectrum is that of $(1-\tau)$, and comparison is made based upon the formula:

$$(1-\tau) = 1 - exp[-(k_s + k_g + NAQ_{ext})L],$$

wherein $\tau$ is the transmittance or fraction of radiation transmitted, and is equal to the (wavenumber-dependent) ratio of measured intensities, with and without particles in the impinging beam (i.e., $I/I_o$). Preferably, the gaseous suspension will be contained in a chamber, and the aperture size of the optical access port, beyond the zone of impingement of the beam upon the particles, will be varied to maximize the dependency of the intensity of collected radiation upon the wavenumbers of the radiation of the impinging beam. In this manner, the curve of the representative spectrum will be optimized for fitting to the curves of preestablished spectra.

BRIEF DESCRIPTION OF THE DRAWINGS

FIG. 1b is a schematic representation of a disc for providing a variable size aperture, suitable for use in the system of FIG. 1a;

FIG. 1c is a schematic representation of a plate suitable for use as diverter in the system of FIG. 1a;

DETAILED DESCRIPTION OF THE ILLUSTRATED AND PREFERRED EMBODIMENTS

Figure 1A:
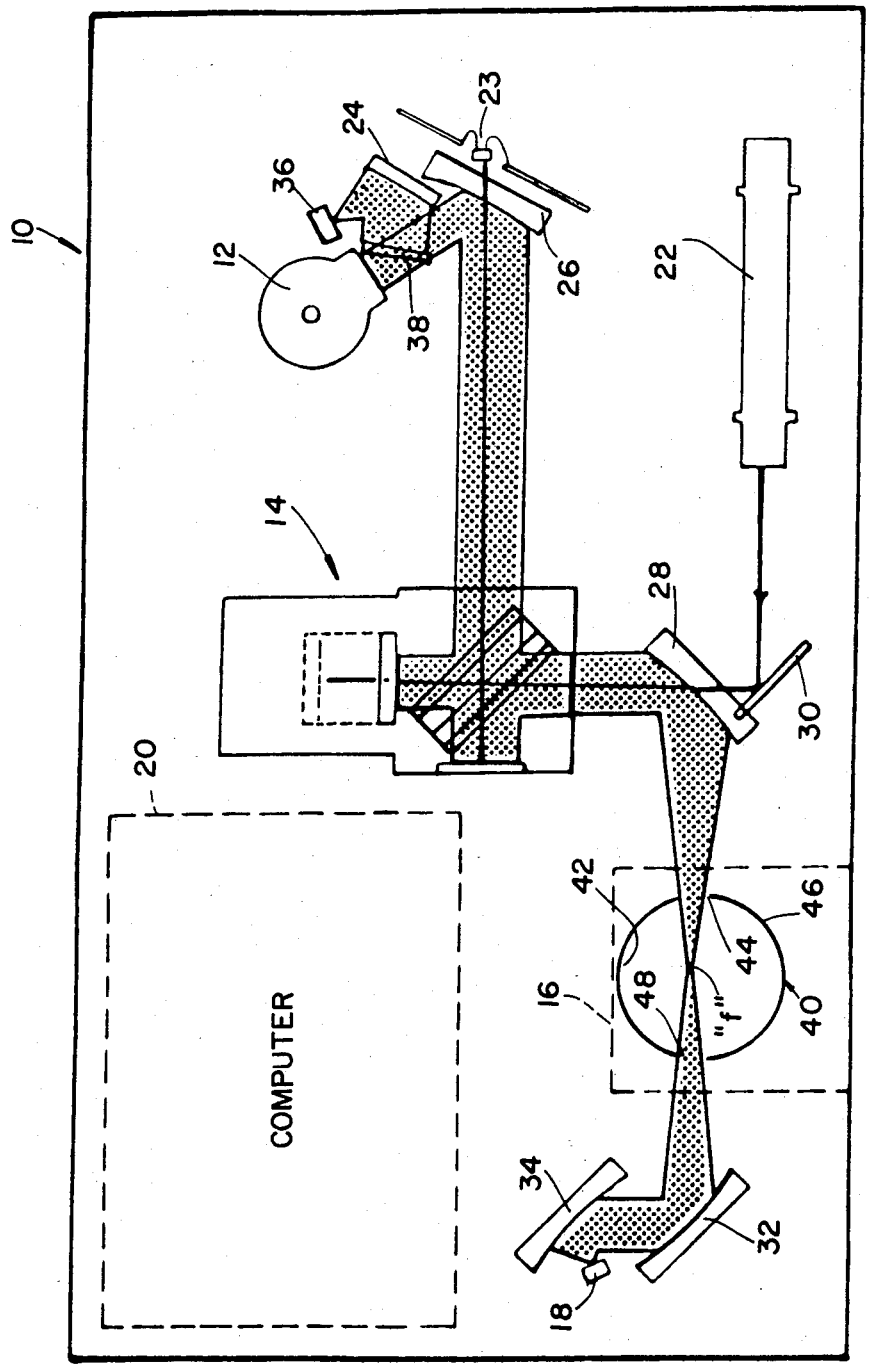
FIG. 1a is a schematic representation of a spectrometric system embodying the present invention.

Turning now in detail to FIG. 1a of the appended drawings, as indicated above the measurement of particle properties is preferably performed, using Fourier-transform infrared spectrometer (FT-IR) apparatus, generally designated by the numeral 10 therein, fitted with special optics and programmed to carry out the unique analysis methodology of the invention. More specifically, the FT-IR apparatus shown schematically in FIG. 1a can be any of several commercially available instruments (e.g., the NICOLET 7199 system), and will include an infrared source 12 (e.g., a globar), a Michelson interferometer, generally designated by the numeral 14, a sample compartment 16, a radiation collector or detector 18, and a computer 20, suitably interconnected (by means not shown) for instrument control and data processing and analysis; it will normally also incorporate a laser beam source 22 and detector 23, for timing purposes. Generally, the spectrometer will be capable of spectral resolution between 0.5 to 8 wavenumbers and of operating at any appropriate scan frequency and any frequency range, although 400–10,000 wavenumbers is preferred. In addition to providing suitable mirrors 24, 26, 28, 30, 32 and 34 at appropriate locations within the system, a second detector 36, a reflective diverter 38, and a sample cell, generally designated by the numeral 40, are incorporated in the illustrated embodiment.

Figure 1B:
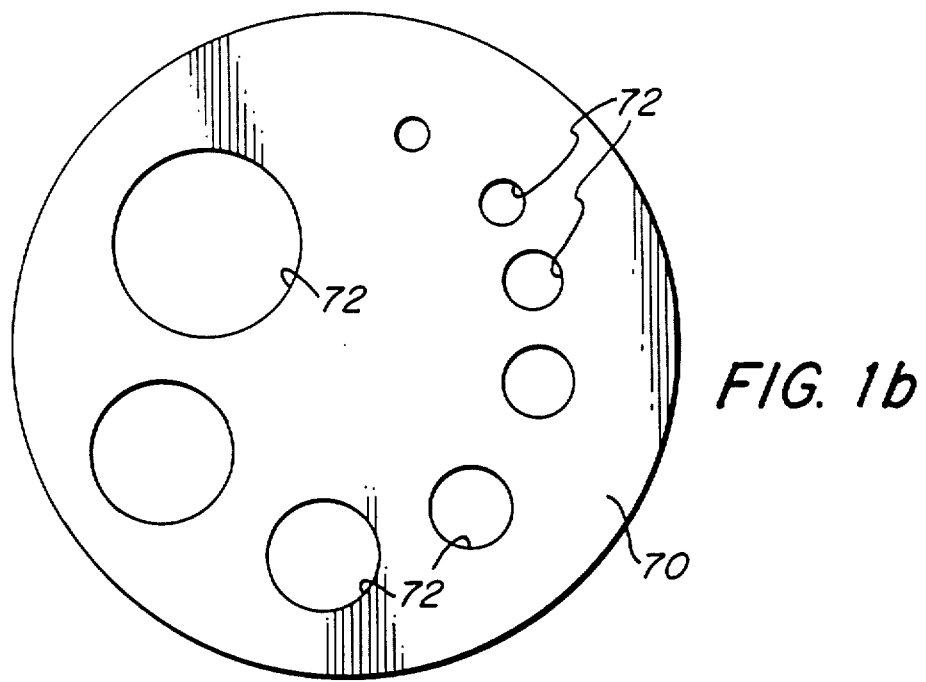

By way of broad description, assuming a measurement of transmitted radiation is to be made for a gaseous suspension passing through the chamber 42 of the cell 40, the IR beam from source 12 is reflected by mirror 26 into the interferometer 14 for encoding. From the interferometer, it is reflected by focusing mirror 28 through port 44 in one side of the cell wall 46, and is brought to a focal volume "f" therewithin. Those components of the beam that are transmitted by the suspension pass through the second port 48 (laterally aligned with the first) in the wall 46, and are reflected by mirrors 32, 34 into the detector 18, which will be selectively adapted to collect the encoded radiation. It should be pointed out that the port 48, which lies beyond the focal zone f (or the zone of particle/beam interaction, if an unfocused beam is employed) with respect to the source 12, may have associated means for varying the size of its aperture, so as to permit adjustments to be made to achieve optimal sensitivity for particle size measurement;

As shown in FIG. 1b, such means may for example take the form of a disc 70 having a series of circular openings 72 of graduated size thereabout, the disc being rotated to align any of them with the port 48.

Radiation emanating from the cell 40 can be collected by the detector 36, being reflected by mirror 28 through the interferometer 14 and encoded for that purpose. To do so, the diverter 38 is positioned (as shown) in the path of the beam reflected from the mirror 26, and will serve to reflect it to the mirror 24 and to the detector 36 therefrom; as will be appreciated, in the embodiment shown the diverter 38 will be displaced (such as by pivoting) from the path of the beam generated by source 12, to permit the above-described transmission measurement to be made.

Figure 1C:
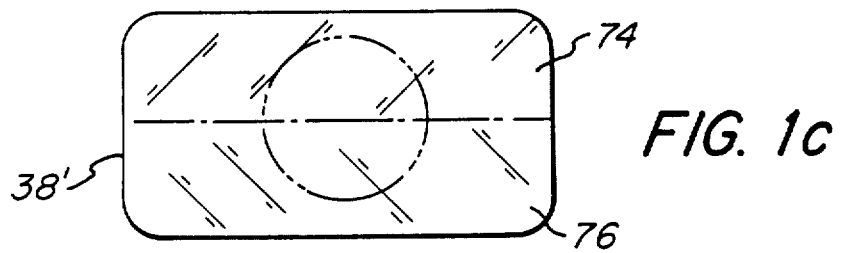

The two measurements (i.e., of transmitted and emanating radiation) can be made sequentially with the arrangement illustrated by rapidly shifting the position of the diverter 38, as indicated. Alternatively, the measurements can be effected simultaneously, and this will normally be the preferred mode of operation. Simultaneous measurements can be made by use of a diverter having two zones of different optical properties disposed in the radiation path, one zone being constructed to pass the beam from the source 12, and the other being made to reflect radiation emanating from the cell 40, which is directed thereto by the mirrors 28 and 26. Such a diverter, 38', is schematically illustrated in FIG. 1c, and takes the form of a plate having a mirrored, upper section 74 and a transparent lower section 86 (the radiation beam circumference being shown in phantom line).

Other arrangements and apparatus features can of course also be employed. For example, since it is desirable in most instances to utilize suspensions in which the particles are homogeneously dispersed, suitable means for providing such suspensions doing so may be included. The apparatus may employ a system of flipping mirrors for projecting the radiation to a common detector location (which may itself comprise a single collector, if appropriately constructed and coupled with suitable analytical data processing logic to perform the desired functions). It is also possible to use only a single optical access port with an aligned reflector, in which case the beam will enter and exit from the same aperture and provide a double-length transmittance measurement through the sample. Moreover, although infrared spectrometry is described and is preferred, other radiation frequencies may be substituted.

It should be appreciated that apparatus such as that of FIG. 1 can be employed, as well, to analyze gaseous suspensions at locations external to the system; e.g., for the in-situ monitoring of a chemical reaction in progress. In those instances the cell 40 would not be used, its functions instead being performed by the on-site containment means (e.g., the reaction vessel), which would of course have suitable ports for optical access, and the mirrors 28, 32 would be positioned (as necessary) to accommodate the reaction vessel therebetween. It is also possible to employ the apparatus for analysis of unconfined volumes (e.g., of a gaseous combustion mixture flowing from a smokestack or over a container), in which case the medium surrounding the suspension would be the ambient, rather than a cell or reactor wall.

Generally, the function of the sampling cell 40 will be to either conduct gas suspended particles through the beam from the source 12, or to provide a second source of radiation emanating from locations about the gaseous stream (e.g., the wall surface 42); as is evidenced by FIG. 1a, moreover, the cell may serve both functions. Because the port 48, which is aligned with port 44 on the optical path, provides an unheated area on the surface 42, it will effectively represent a gap in the radiation source surrounding the particle flow path, and will thereby limit the components collected from that source to those which are refracted or otherwise scattered by the particles into the optics of detector 36. Obviously, the same effect could be achieved by other means in the absence of a port, such as by cooling the corresponding, on-axis area of the wall. If a transmission beam were projected through port 48 toward port 44, that fraction of its rays which was not scattered out of the optical path would of course be directed toward the same detector; however, the coding effects provided by the apparatus permit them to be discriminated, so as to not contribute to the refracted radiation measurement. In the particular arrangement of FIG. 1a, such coding permits the detector 18 to discriminate and collect the rays from the source 12 which are transmitted through the particles, and permits the detector 36 to do the same with regard to the radiation emanating from the cell 40.

In any event, the geometry of the cell should be such that no appreciable attenuation of the IR beam occurs in traversing it from port 44 to port 48 unless particles are present, generally within a volume of focus thereof.

Similarly, it should be so designed that no appreciable radiation from the second radiation source (e.g., surface 42) reaches detector 36 in the absence of particles in such a zone of the optical path.

Figure 2:
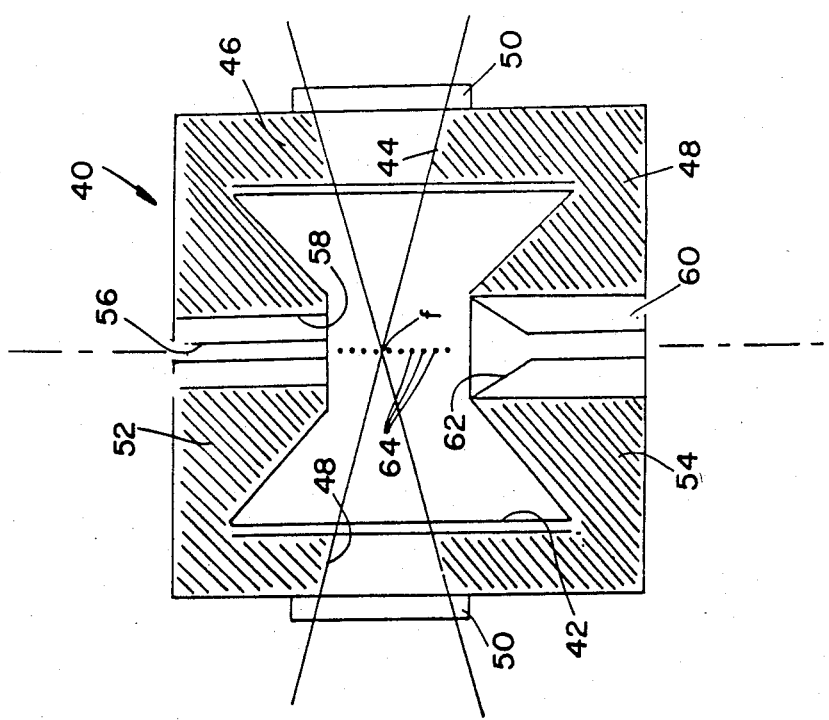
FIG. 2 is a schematic representation of a sampling cell appropriate for use in the system of FIG. 1.

A preferred embodiment of the sampling cell 40 is schematically illustrated in FIG. 2. It consists of a body 48 having an internal cavity 42 of circular cross section, defined by the inside surface of wall 46. Means 47 is provided for controlling the temperature of the wall surface (normally, the heated section will be separate from the remainder of the wall 46, to minimize heat loss and energy requirements), and ports 44, 48 are aligned diametrically on the opposite sides of the wall 46 and provide optical access to the cavity 42; the ports are closed by transparent windows 50. Passages in the top and bottom walls 52, 54, respectively, of the body 48 are aligned on the longitudinal axis of the wall 46, and are constructed to provide particle injection and collection features for the cell.

More specifically, the injection feature is provided by two coaxial tubular conduits, the inner conduit being temperature controlled by means 47 and providing a channel 56 for the gaseous suspension of particles to be injected into the cell, and the outer conduit providing a channel 58, of annular cross section, for delivery of a gas which is to form a sheath about the suspension. The collection feature is provided by an insert 60, which is also temperature controlled by means 47 having a funnel-like conduit 62 formed therethrough.

As can be seen, the optical path of the spectrometer beam traverses the ports 44, 48, and is brought to a focal zone at "f", within the cavity 42. The particles 64 are injected through the conduit 56 (in monodispersed form, in the illustrated embodiment), into the focal volume of the beam for interaction therewith, and are thereafter removed from the cell through the conduit 62.

The design of the illustrated cell serves to minimize any path for radiation to enter the emission detector 36 in the absence of a sample stream. It will be appreciated that the fluid mechanics will be so designed so that the sample stream will pass through the cavity virtually without loss and without appreciable alteration of its temperature, by internal cavity radiation, when the temperature controlled walls are hot (relative to the particles). Moreover, under those conditions the gas velocity must be sufficiently high to avoid particle heating; flow velocities of 1–100 meters/second will generally be employed, and residence times will typically range from fractions of a millisecond to about one-tenth second.

The carrier gas used can be of any desired composition; nitrogen and argon will be beneficial in providing a non-reactive environment which will not interfere in the IR spectra. On the other hand, the use of "tracer" gases which exhibit IR absorption, such as carbon monoxide, will allow for gas temperature diagnostics. The sheath gas can be nitrogen, argon, or other non-absorbing gas. The suspended particles can, as explained above, be solids, including very finely divided substances such as soot, or liquid droplets; optimally, the particles will be less than 300 micrometers in diameter, and they can be either monodispersed or polydispersed in the gas phase.

The Measurements

Generally, the analysis methodology will consist of obtaining transmittance spectra, emission spectra, or both, which preferably (particularly for the sake of speed and accuracy) will be taken simultaneously, and under conditions ensuring homogeneity of the particle concentration in the gas phase. These spectra are obtained and analyzed with an FT-IR spectrometer under computer control, using special computer software functionally described herein to determine desired parameters and properties of the particles.

For purposes of calibration, spectra are obtained in the absence of a sample stream. Normally, calibration will be required only at infrequent intervals, depending of course upon the stability of the optical system and detectors.

Emission Measurements

The emission measurements require that a wavenumber dependent instrument response function, $F_\nu$, be determined for each resolution used. This is done by obtaining a spectrum "$R_\nu$" (using a detector such as 36 in FIG. 1a), from a reference black-body placed at the focal point "f". $R_\nu$ is corrected by subtracting the background with no source present, and is divided by the black-body curve "$BB(T_R)$" appropriate to the temperature of the reference; thus, the response function is determined in accordance with the formula:

$$F_\nu = R_\nu / BB(T_R)$$

It should be appreciated that all of the above quantities are wavenumber dependent, and that the measured spectral response curve will be obtained with a collector such as the so-called "MCT", "InSb" or "TGS" detectors. Instrument response functions and background spectra were observed to be stable over several weeks, provided that cell conditions remained constant.

A sample emission spectrum "E" is then obtained by dividing (using the computer associated with the spectrometer) the observed spectrum "O" at the detector, with particles present in the focus "f" and corrected for background, by the instrument response function F (the subscript "$\nu$" is omitted for convenience). It has been found that emission measurements, with appropriate background and instrument response corrections, were made with good signal-to-noise ratios, in as little as 200 milliseconds. Examples of such data are shown in FIGS. 5a–8d (in which radiance is plotted against wavenumber) for a number of cases where the particles are of different composition and at different temperatures with respect to the wall.

Absorption Measurements

Measurements of absorption, or transmittance, are made in the normal way. The spectrum from a globar source [see Bohren, C. F. and Huffman, D. R., "Absorption and Scattering of Light by Small Particles", John Wiley and Sons, New York, NY (1983)] passing through the empty cell is measured to determine intensity "$I_o$" at each wavenumber, and the same measurement is made with the particles in the cell to give the intensity "I". As indicated above, the transmittance "$\tau$" is defined as the fraction of the radiation transmitted ($\tau = I/I_o$), which term is also used herein to refer to the transmitted percentage. The absorbance "A" is given by $A = -\log_{10} \tau$, and the fraction percentage of radiation absorbed and scattered is given by $(1-\tau)$.

Figure 9A:
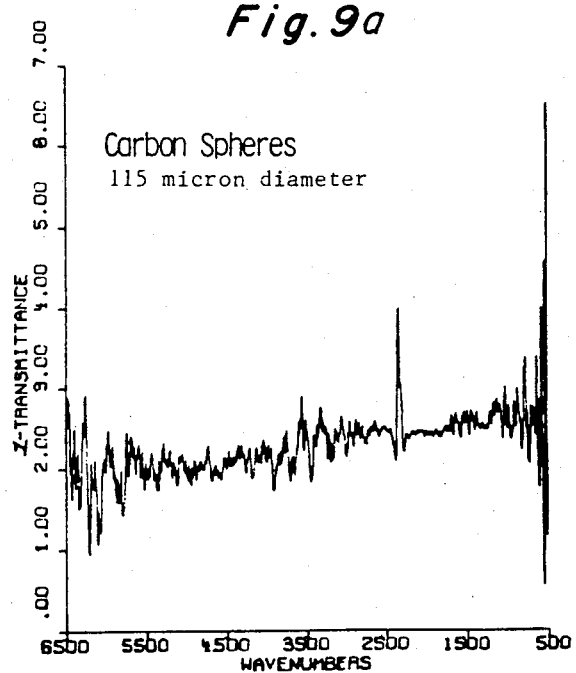
Figure 9C:
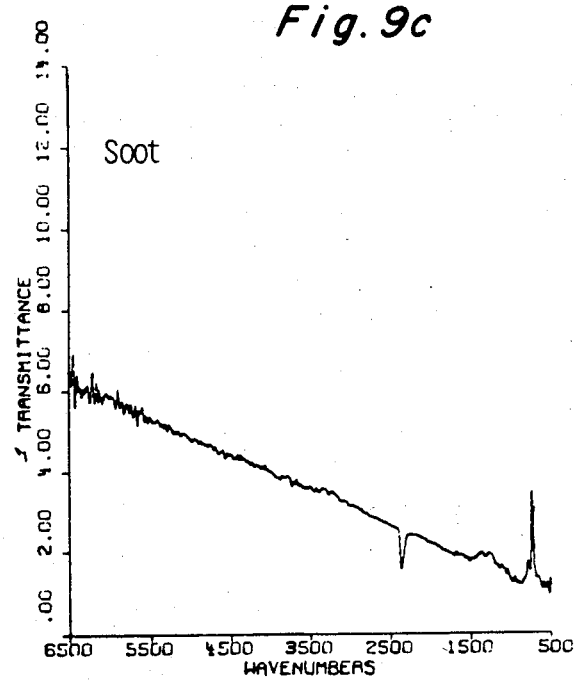
Figure 9B:
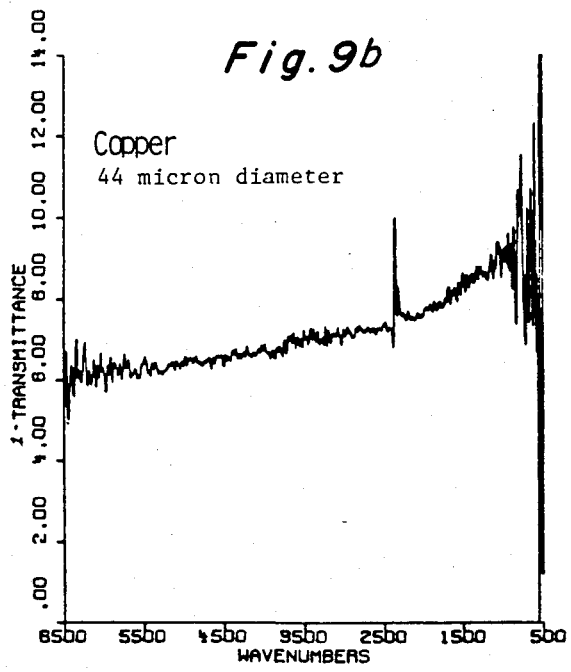
Figure 9D:
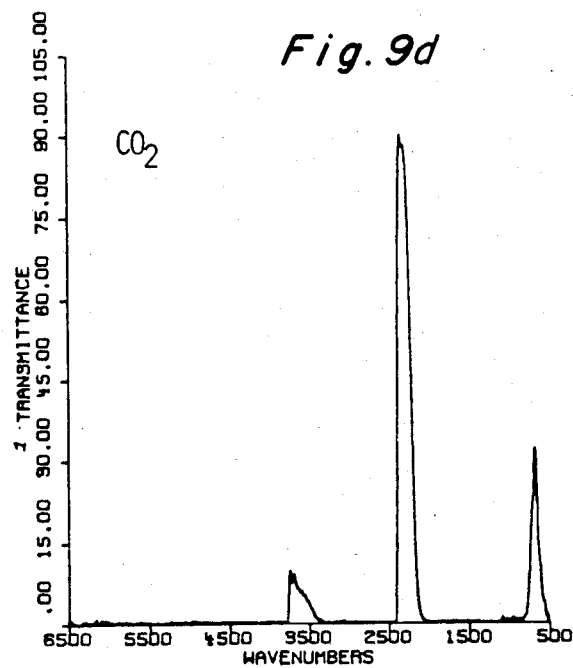
Figure 10A:
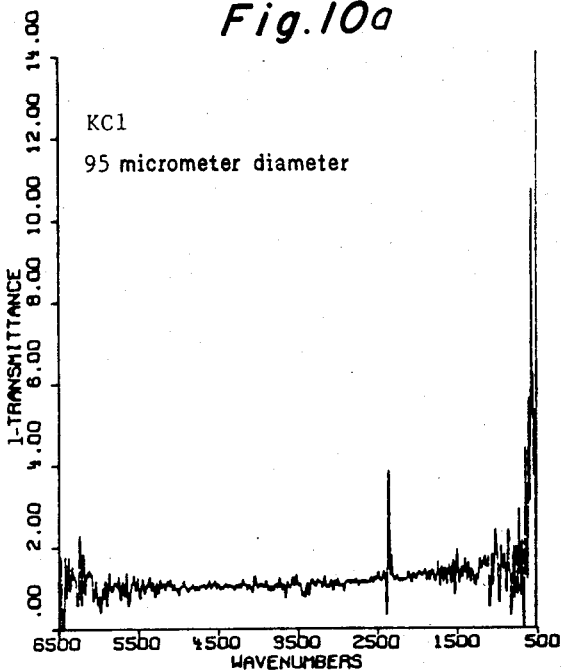
Figure 10C:
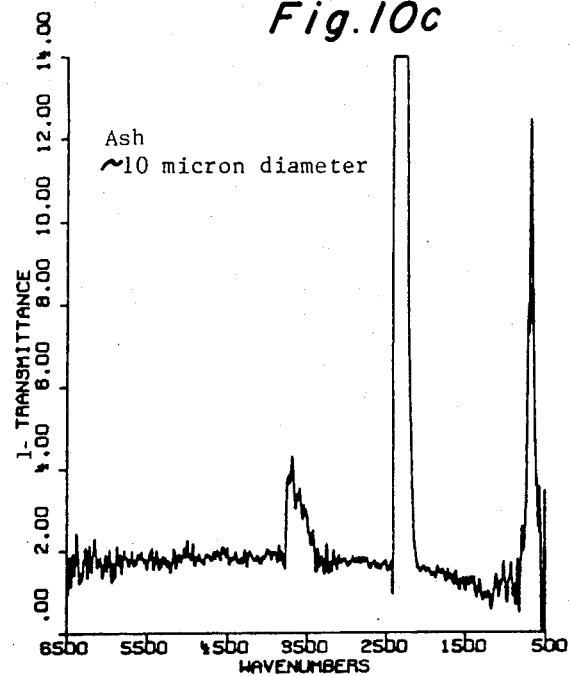
Figure 10B:
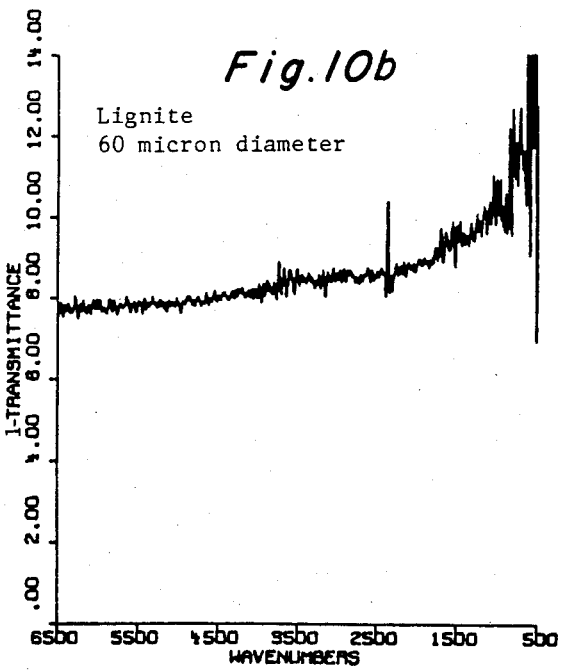
Figure 10D:
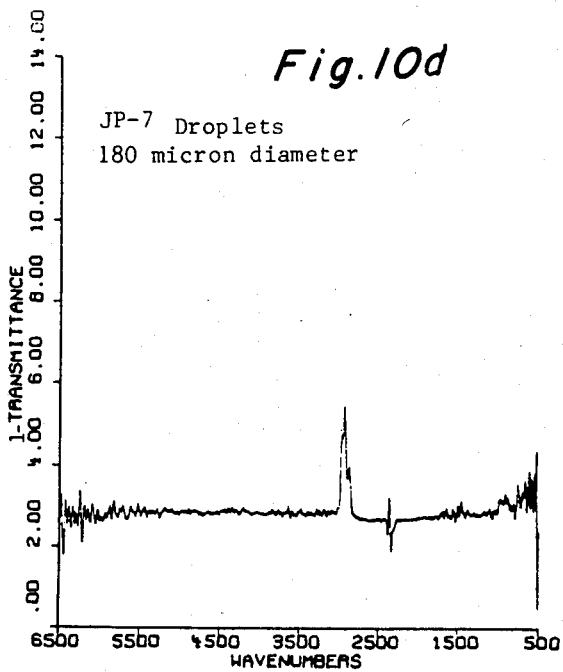
Figure 11A:
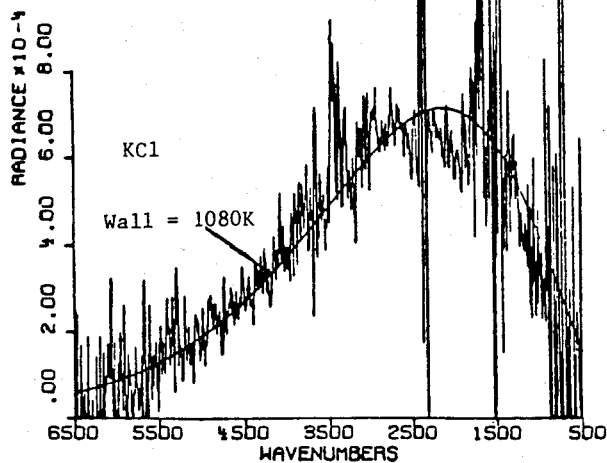
Figure 11C:
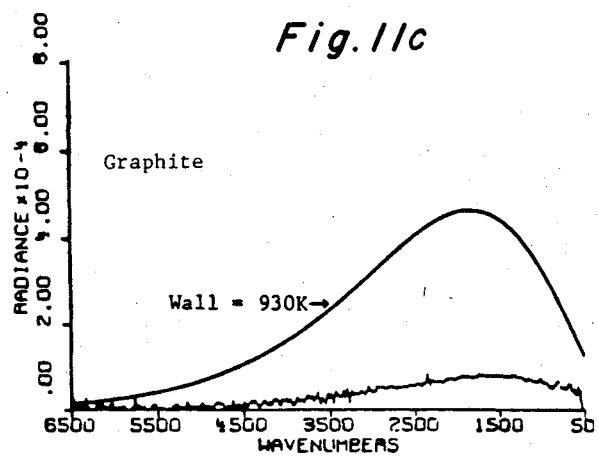
Figure 11B:
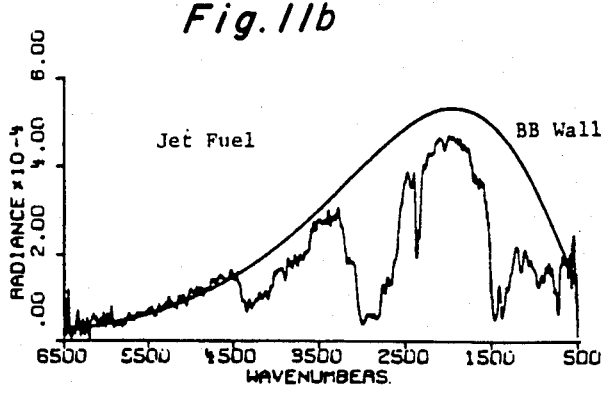
Figure 11D:
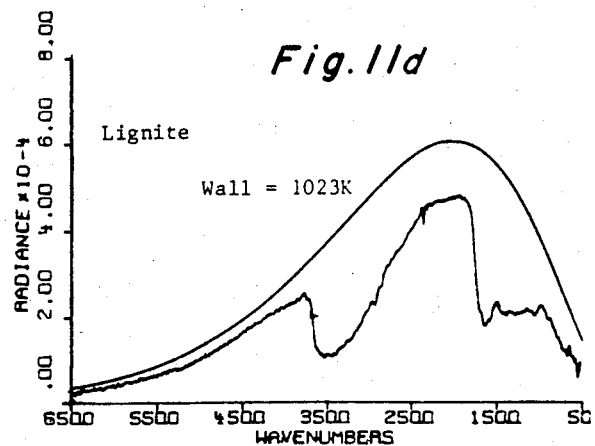

Examples of the transmission, plotted as $(1-\tau)$ as a function of wavenumber, are presented in FIGS. 9a–d and 10a–d. FIGS. 9a and 9b are for carbon and copper particles. Particles can of course block radiation by absorption and by scattering (i.e., reflection, refraction and diffraction). For particles of diameter greater than several micrometers, and for wavelengths of present interest (e. g., 1.6 to 25 micrometers), it has been predicted and observed, in accordance herewith, that almost none of the incident radiation is transmitted directly through the particle along its original rectilinear path. This is true even for particles that are completely or partially transparent in the infrared range, such as potassium chloride (FIG. 10a) and fuel oil (10d), as long as the refractive index of the substance differs from unity. In addition, diffraction and interference can produce a wavelength-dependent reduction of the transmitted intensity by a factor that is as much as twice the projected area of the particle (see Hottel, H. C. and A. F., "Radiative Transfer", McGraw-Hill Company, New York, (1976) and van de Hulst, H. C., "Light Scattering by Small Particles":, Dover Publications, NY, (1981).] in addition to the Bohren and Huffman reference noted above).

With regard to FIGS. 9a and 9b, it is expected that particles such as carbon and copper block radiation over their projected surface area at relatively short wavelengths (large wavenumbers), with diffraction effects decreasing the transmission at longer wavelength values. For large particles, therefore, $(1-\tau)$ at short wavelengths is taken as a measure of the fraction of the viewing area which is blocked by the projected area thereof. For soot particles, of diameter 0.1 micrometer (FIG. 9c), the level of absorption is highly dependent upon wavelength, decreasing at longer values.

An FT-IR spectrometer is ideally suited for making transmission measurements in a hot cell, since the detector will only record radiation which has been modulated by the Michelson interferometer and will therefore reject radiation originating at the hot cell walls. Of course, such a spectrometer also offers the advantages of high sensitivity, high resolution, and rapid scan in all applications, and is therefore the preferred apparatus herein, and the apparatus of first choice in the practice of the instant method.

Normalized Emission

In analyzing the data from the measurements made, the determination of radiation extinction by the particles, relative to their blocking area, is of primary interest. This is done by use of "normalized" emission "$E_n$", equal to $E/(1-\tau)$. Examples of normalized emission for several cases of interest are presented in FIGS. 11a to 14d (plots of radiance versus wavenumber). As can be seen, the spectra vary substantially with the composition of the particles and their temperature relative to the cell wall.

The Analyses

Analysis of Size and Density

To determine the size and concentration (number density) of the particles in the suspension analyzed, transmittance spectra are employed, examples of which, plotted as $(1-\tau)$, are presented in FIGS. 9a-d and 10a-d. In the case of particles which block less than 20 percent of the transmitted light, the quantity $(1-\tau)$ is approximately equal to the quantity $Q_{ext}$ NAL, and can readily be evaluated in accordance herewith; when blockage is greater than 20 percent, valuable information can still be obtained, but the analysis is considerably more complex. For a spectrometer acceptance angle of $\theta$, and particles with perimeter "P" such that $(P/\lambda)(\sin\theta)$ is equal to or less than 3, diffraction and interference can produce a wavelength-dependent reduction of the transmitted intensity which is as much as twice the fractional projected area. An example of this phenomenon, which is well understood, is illustrated in FIG. 9b, which shows enhanced scattering at long wavelengths. For purposes of the present analysis, the FT-IR spectrometer used had an acceptance angle of 0.25 radian.

Figure 15:
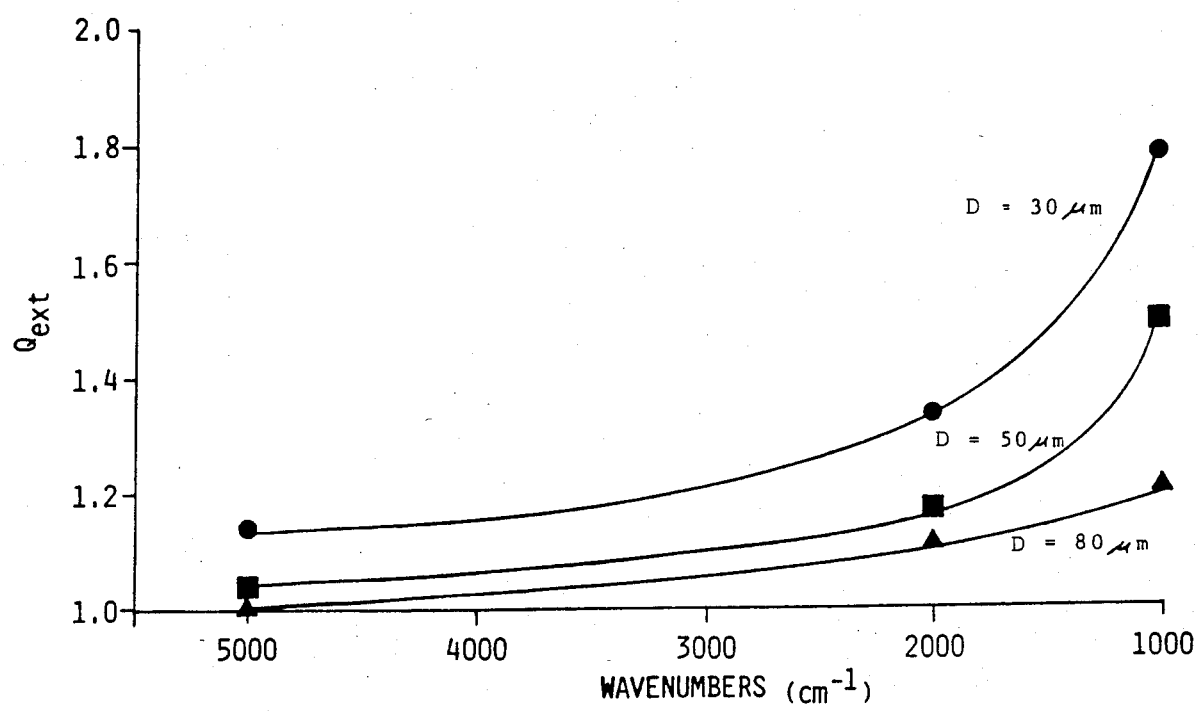

While the full Mie scattering theory is available to treat the effect of diffraction, the simpler Rayleigh expression has been employed herein, which has been shown to be accurate for the larger P/λ ratios (see Gumbrecht, R. O. and Sliepcevich, C. N., *J. Phys. Chem.* 57, 90 (1953).] For FIGS. 9a and 9b, it is expected that the particles block radiation over their projected surface area at relatively short wavelengths (large wavenumbers) with diffraction effects decreasing the transmittance further at longer wavelengths. Therefore, for large particles the expression "$(1-\tau)$" at short wavelengths is a measure of the fraction of the viewing area which is blocked by the particles, while the shape of $(1-\tau)$ is a measure of the particle size. FIG. 15 illustrates the calculated shapes of three different sizes.

By way of specific example, the diameters of particles monodispersed in a gas stream, traversing a cell in a system such as illustrated in FIG. 1a, is obtained by a least squares fitting routine, which compares $(1-\tau)$ to theoretical curves. Least squares fitting is a technique which seeks, such as through successive approximations, to minimize the value of the square of the difference between the actual and the computed values for a particular selected parameter. This operation may be conducted iteratively until an acceptable minimization occurs, whereupon those particular values of the parameters are outputted, as providing the best fit.

Comparing the theoretical predictions to the curves of FIGS. 9a-d and 10a-d gives the following average particle sizes for the several substances: carbon spheres (FIG. 9a) 80 micrometers; copper (FIG. 9b) 32 micrometers; potassium chloride (FIG. 10a) 80 micrometers; lignite (FIG. 10b) 56 micrometers; and fuel droplets (FIG. 10d) greater than 100 micrometers. These values are in reasonable agreement with the corresponding values of 115, 44, 95, 60 and 180, respectively, as determined by sieving or photomicroscopy. Because the latter techniques indicate the largest dimensions of the particles, rather than average values, determination by $(1-\tau)$ plotting would be expected to give smaller particle size indications, as it does.

For mixed sizes, the observed spectrum is least squares fit to the theoretical prediction for a log-normal (or other) distribution. Range and accuracy can be improved by obtaining additional data for smaller acceptance angles $\theta$, which can be changed by using a variable aperture between the focus "f" and the detector 18. For example, decreasing $\theta$ by a factor of 3 will increase the maximum measurable size to approximately 300 micrometers.

In any event, the fitting routine will provide a determination of $Q_{ext}$ and the average particle diameter (assuming a spherical shape) from which the particle area "A" can be calculated. Then the quantity "N×L" (concentration times path length) is determined from the known quantitites, according to the derived approximation equation set forth above.

Figure 16:
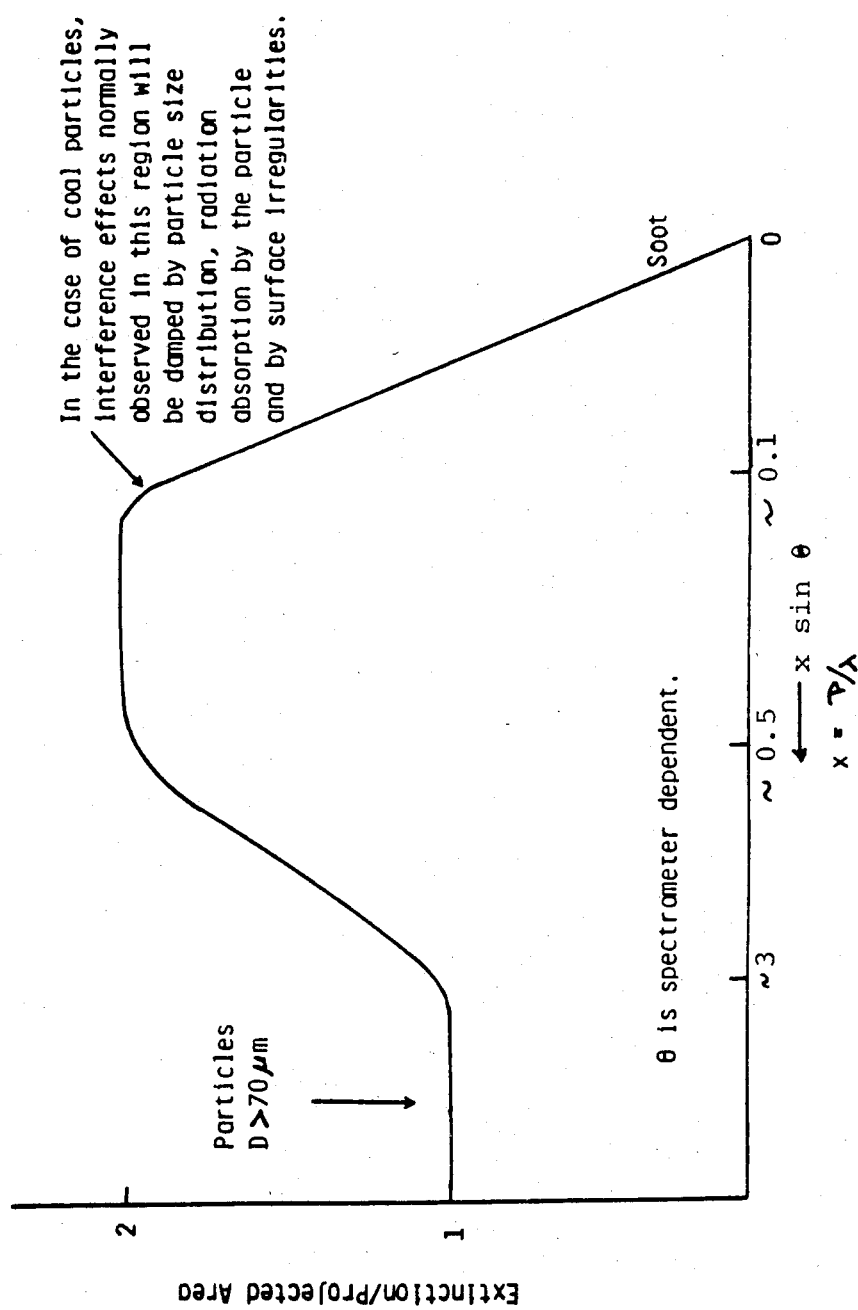

An important factor in analyzing the size distribution for particles has been found to be the value of the extinction of radiation caused by the particles, relative to their blocking area. Extinction of radiation is schematically illustrated in FIG. 16, wherein "$Q_{ext}$" (which, in the preferred embodiments of the invention, depends on the entrance aperture of the FT-IR optics), is plotted against "X" for particles with wavelength-independent optical constants, X being equal to P/λ. In the Figure, the "blocking" region ($Q_{ext}=1$) is on the left. For particles larger than about 100 micrometers, Q is equal to 1 over the whole wavelength region, depending on the value of the refractive index. For smaller particles, Q increases to a maximum value of 2, which effect is observed as an increase in absorption at long wavelengths (see FIGS. 9a and 9b). Also indicated in the diagram is the scattering behavior of very small particles, for which X is less than 1. Small soot particles (see FIG. 9c) and possibly ash particles (FIG. 10c) lie in this range, for the wavelengths of interest for this technique; for such small particles the quantity "$(1-\tau)$" decreases at long wavelengths.

Analysis of Composition

Quantitative analysis of particulate composition is made using the normalized emission function; emission spectra alone can be employed for semi-qualitative analysis. The representative spectra are obtained when the particles are at low temperatures relative to the surrounding medium; ideally, the particle will be near room temperature or below, with the suspension contained in a chamber having a wall surface temperature of 500° Centigrade, or above.

In the simplest case, there will be no effect from gas or soot absorption or radiation; the particle will be assumed to be at a temperature low enough to neglect its emission, and to be large enough to neglect diffraction effects. Under these circumstances, $BB(T_p)$ will be approximately zero, $Q_{ext}$ will equal the quantity $(Q_s+Q_{abs})$ and will have a value of about unity, and $E_n$ will about equal $Q_s$ times the black-body specrum at the temperature of the wall; thus, the general equation for $E_n$, set forth above, will reduce to: $E_n=(1-Q_{abs})BB(T_w)$. In the simple case of potassium chloride, where $Q_{abs}$ is approximately zero (FIG. 11a), $E_n$ equals $BB(T_w)$, which agrees with the observed spectrum.

For samples where $Q_{abs}$ has a value other than zero, the compositional information is contained in the function $E_n$. For example, the absorption bands for coal and fuel oil can be seen in the emission spectra of FIGS. 5a and b, and the normalized emission spectra of FIGS. 11b and 11d. The value of $Q_{abs}$ must be related to the shape and optical properties of the particles.

Figure 3:
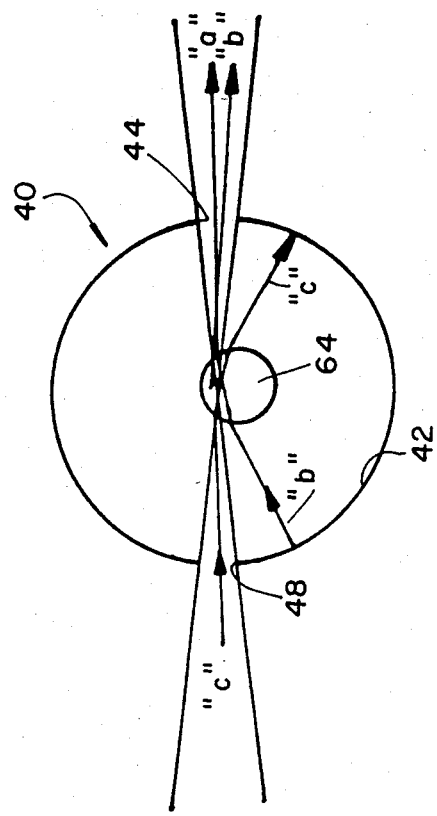
FIG. 3 is a schematic representation showing the geometry of emission and transmission measurements, taken along the axis of the cell.

The various effects which have been observed can be quantitatively explained on the basis of refraction of radiation, as schematically indicated in FIG. 3, which shows the geometry for the emission and transmission measurements, looking down the axis of the cell 40 with a particle 64 at the focus "f" of the FT-IR beam. The emission spectrum consists of actual emission from the particles (ray "a"), plus radiation (ray "b") from the walls which is diffracted (or reflected) from virtually any angle that is oblique to the port 44 (i.e., off the axis between it and the particle) into the collection optics; ray "c" is a component of incident radiation (e.g., a transmission beam) which has been refracted out of the optical path, and scattered to virtually any angle relative thereto.

Figure 5A:
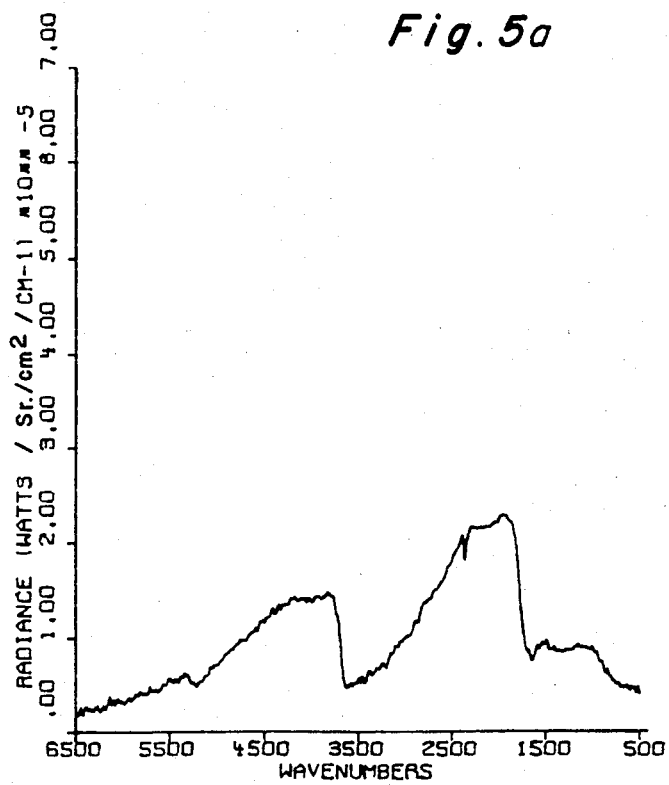
Figure 5B:
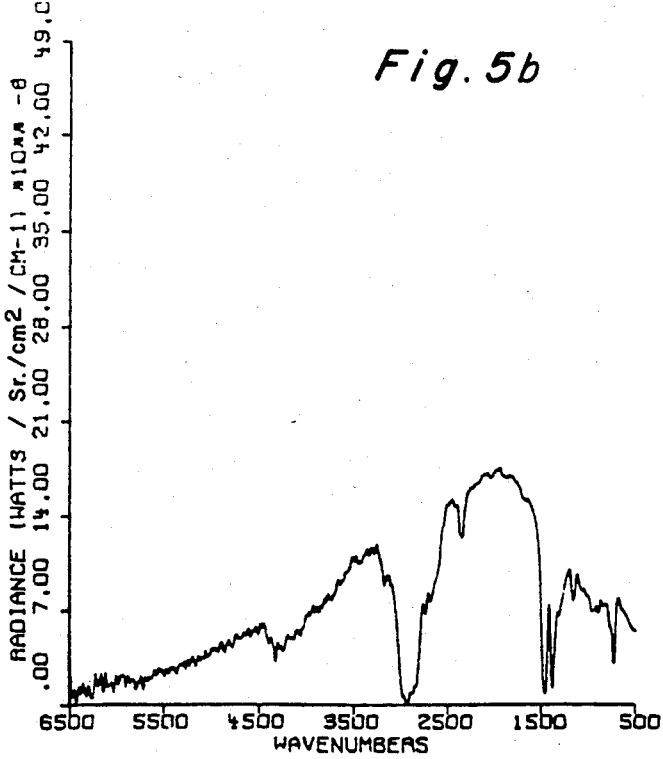
Figure 6A:
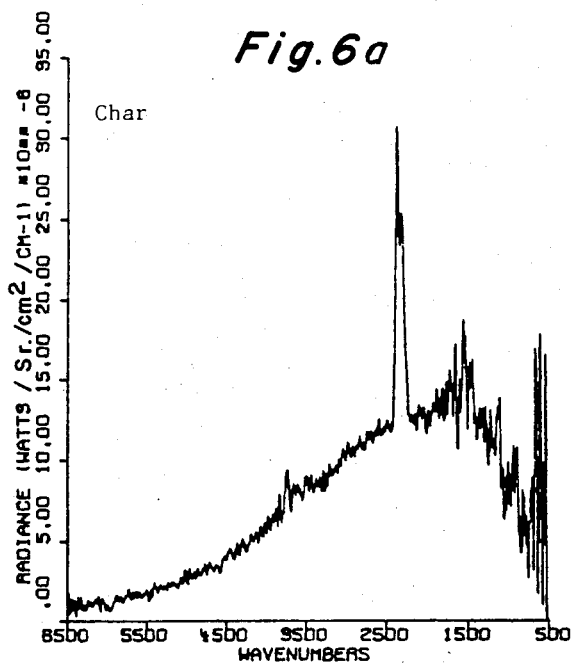
Figure 6C:
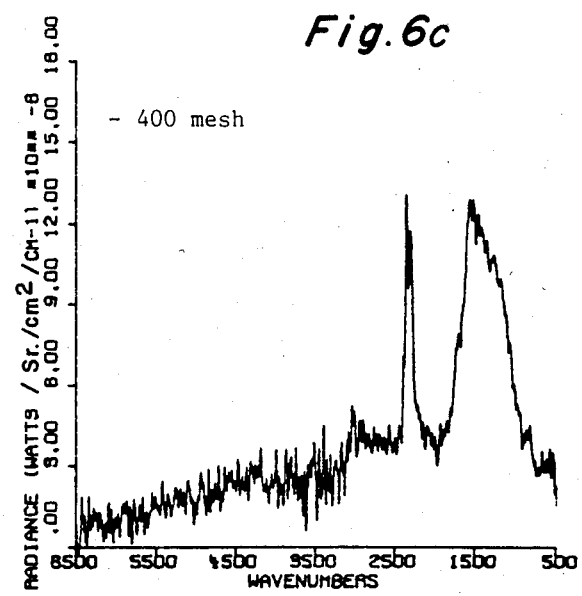
Figure 6B:
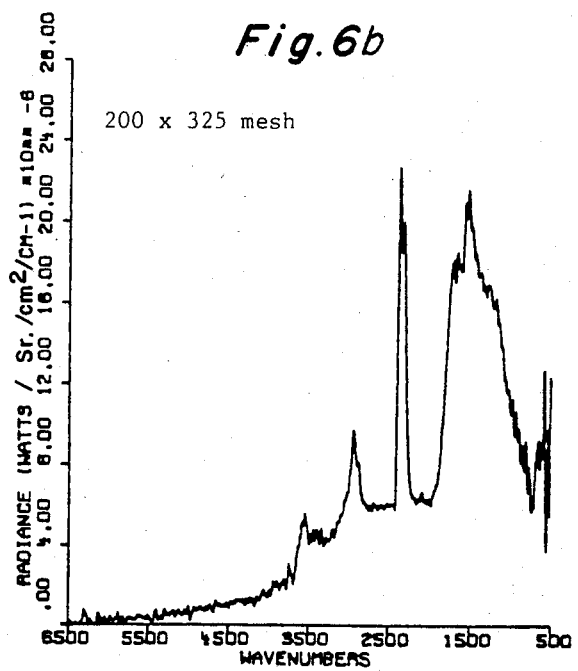
Figure 6D:
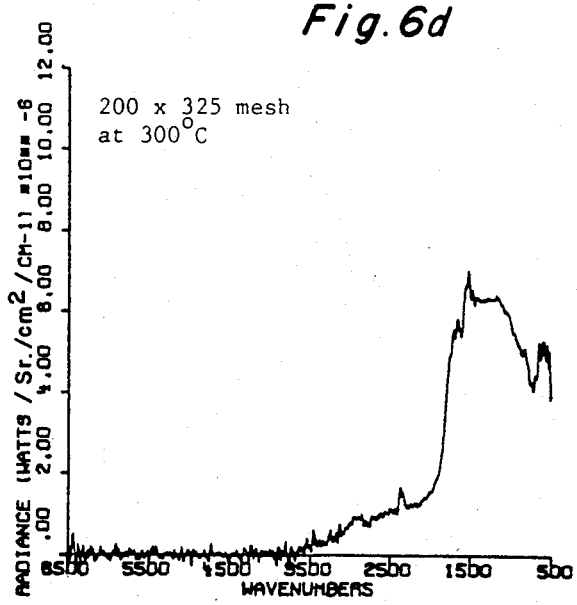
Figure 7A:
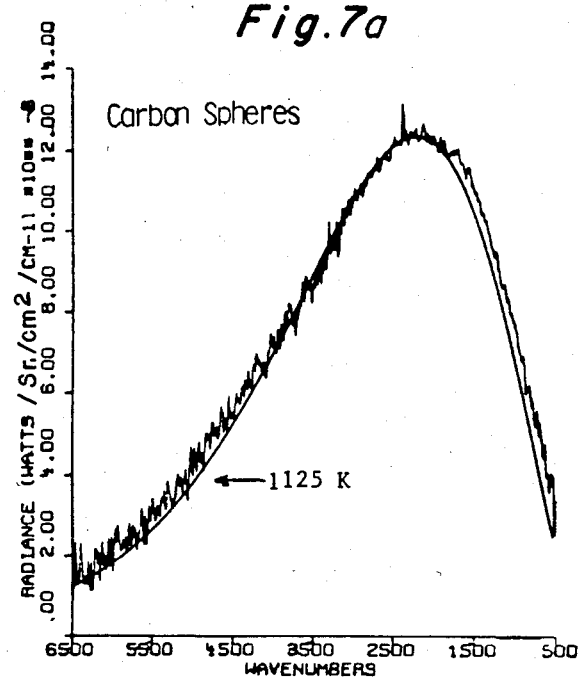
Figure 7C:
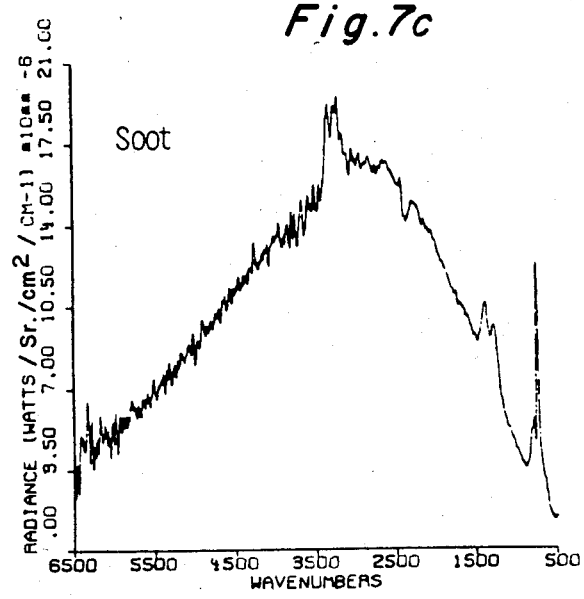
Figure 7B:
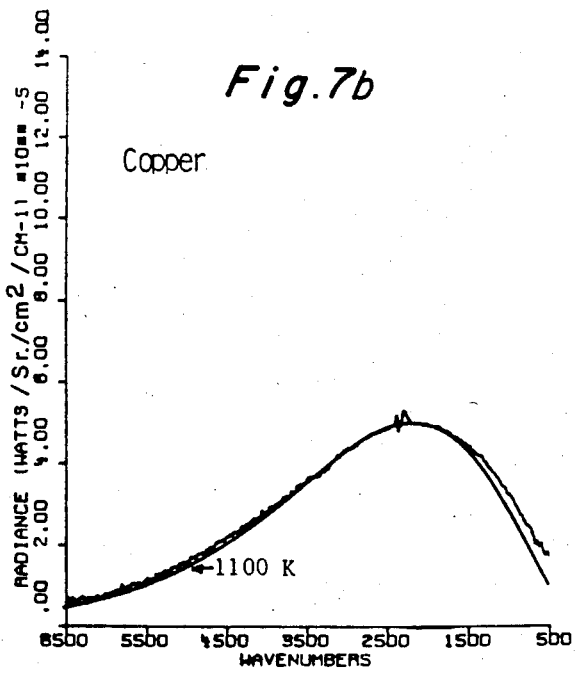
Figure 7D:
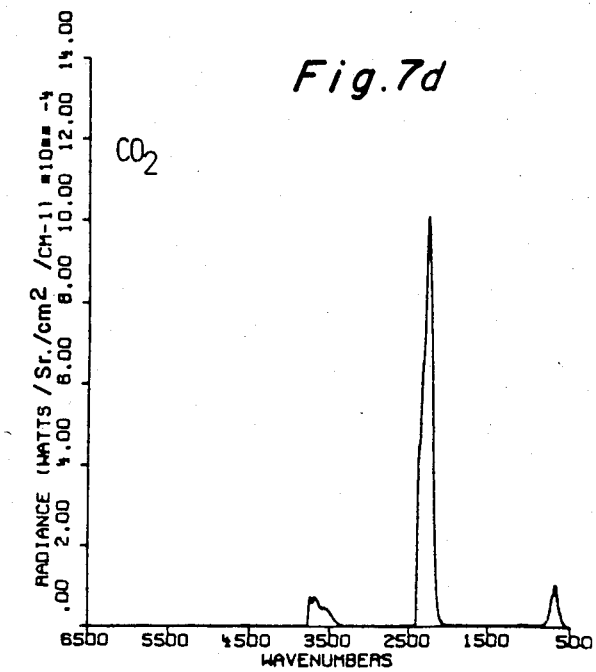
Figure 8A:
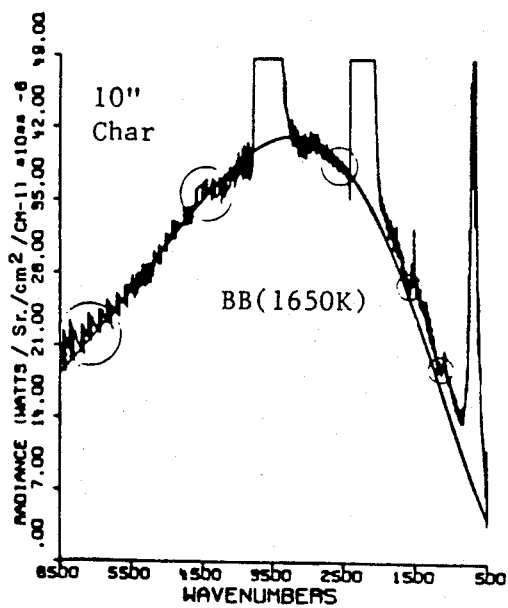
Figure 8C:
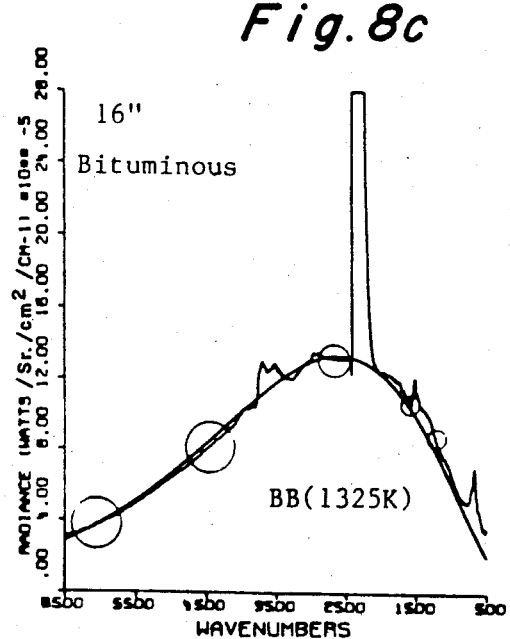
Figure 8B:
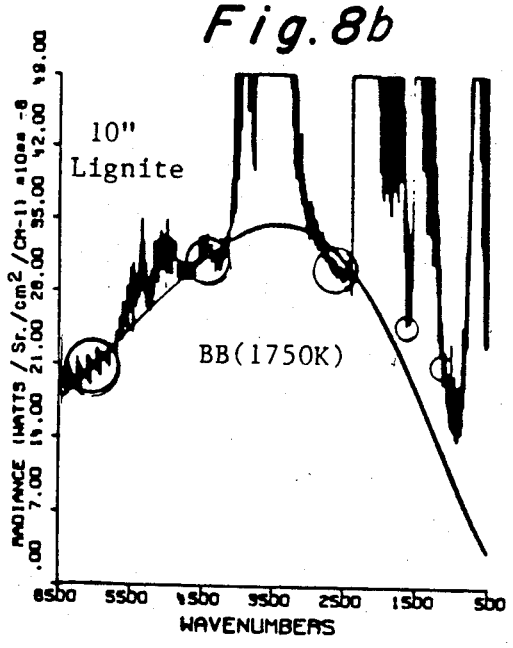
Figure 8D:
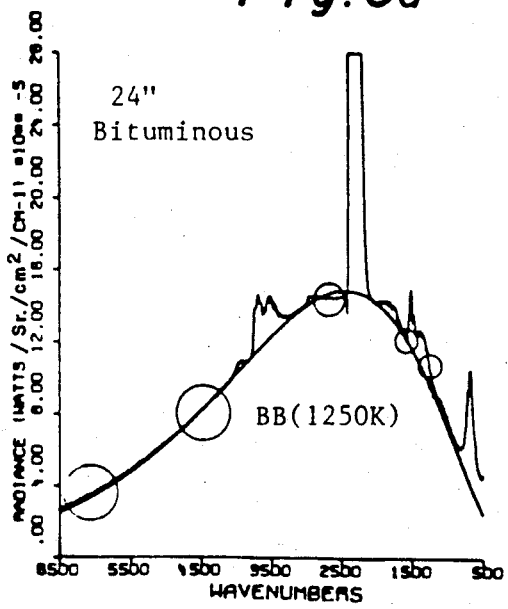

For FIGS. 5a,b and 11a-d, the particles are cold, so only the radiation scattered (diffracted, refracted or reflected) into the collection optics contributes, and the magnitude of the signal will depend on the size of the particle, the index of refraction of the substance, and its absorptivity. For a sphere, exact calculations can be performed to determine absorptivity from $E_n$, given the diameter of the particles, the degree of scattering on the surface, and the index of refraction.

In the simple case of non-reflecting spheres of a substance having an index of refraction greater than 1.5 $Q_{abs}$ is approximately equal to the quantity $(1-e^{-k_\alpha D})$, where $k_\alpha$ is the wavelength dependent absorption coefficient (absorbance) of the sample, and D is the diameter of the sphere, which may be known or computed from $(1-\tau)$ as discussed above. Then, the following derived equation applies:

$$k_\alpha = \frac{-\ln(1-Q_{abs})}{D} = \frac{-\ln(E_n/BB(T_w))}{D}$$

Figure 17A:
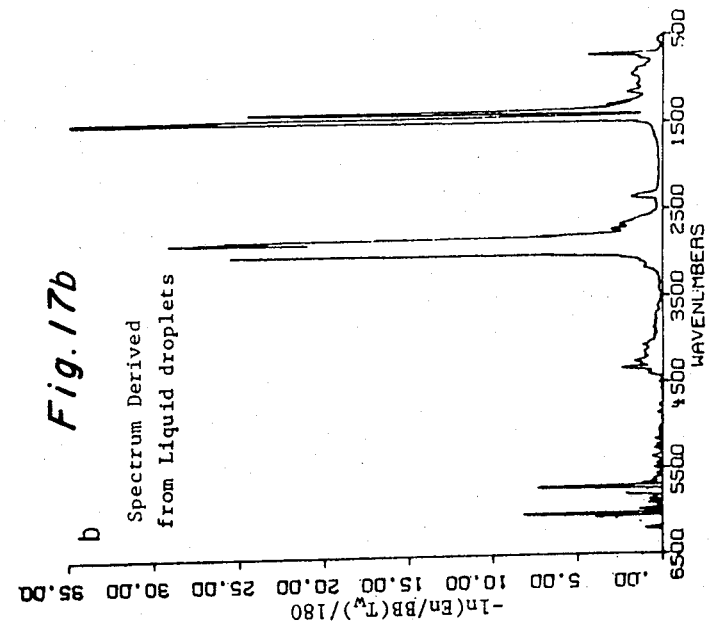
Figure 17B:
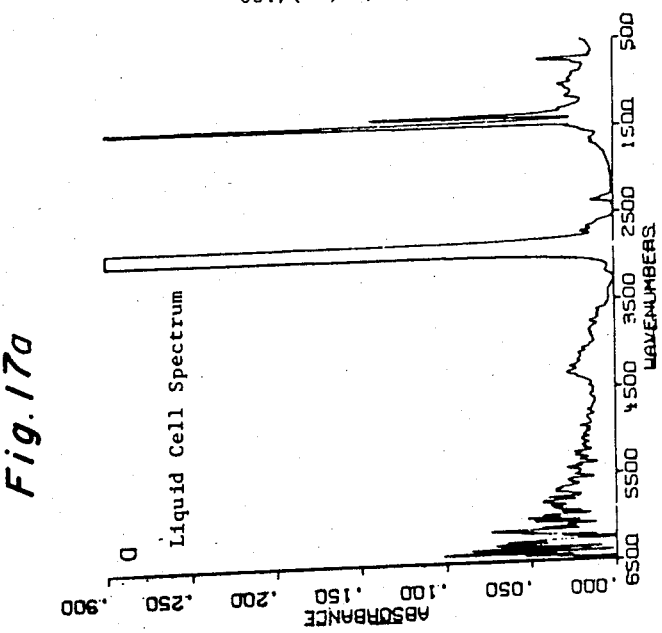

FIGS. 17a and b present a comparison of $k_\alpha$ for a jet fuel composition, computed from the foregoing equation using the observed diameter of 180 micrometers, and measured in a liquid cell, respectively; it can be seen that the agreement is excellent.

As indicated above, semi-quantitative spectra can be obtained using emission spectra alone, such as those shown in FIGS. 5a,b. For that purpose, $BB(T_W)$ may be scaled to fit the highest regions of the emission spectra.

Analysis of Emittance

The spectral emittance of particles can be made either with them cooler or hotter than the surrounding medium (the particles can be heated, for example, in a heated injector, an entrained flow reactor or a heated tube reactor associated with the analytical apparatus). The simplest case is for large particles ($Q_{ext}=1$), where the particle temperature is greater than that of the envirous ($T_p>T_w$), and where soot and absorbing gases are absent ($k_s=k_g=0$). Under those conditions, $E_n=\epsilon BB(T_p)$ and, conversely, $\epsilon=E_n/BB(T_p)$.

To determine $\epsilon$, measurements were made in a cell with a temperature controlled injector heating the particles to a known equlibrium temperature $T_p$. Examples of $E_n$ and $BB(T_p)$ for char and lignite particles of two size cuts, at different temperatures, are presented in FIGS. 12a-d. The emittance varies with the degree of pyrolysis and particle size.

Figure 12A:
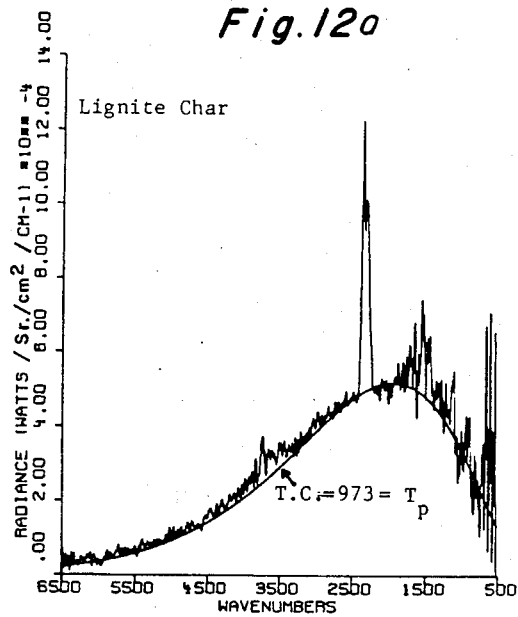
Figure 12B:
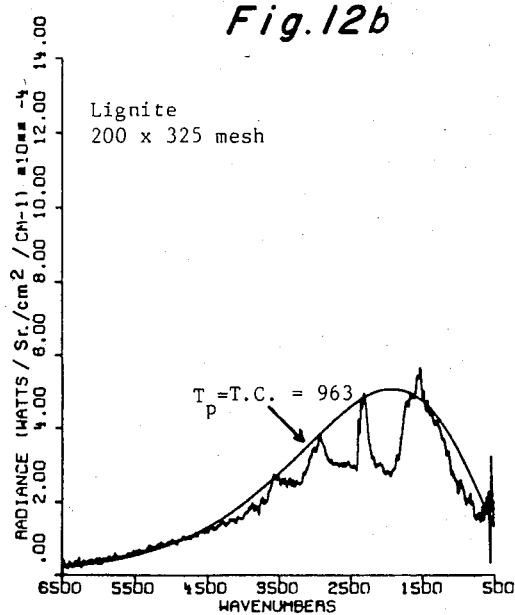
Figure 12C:
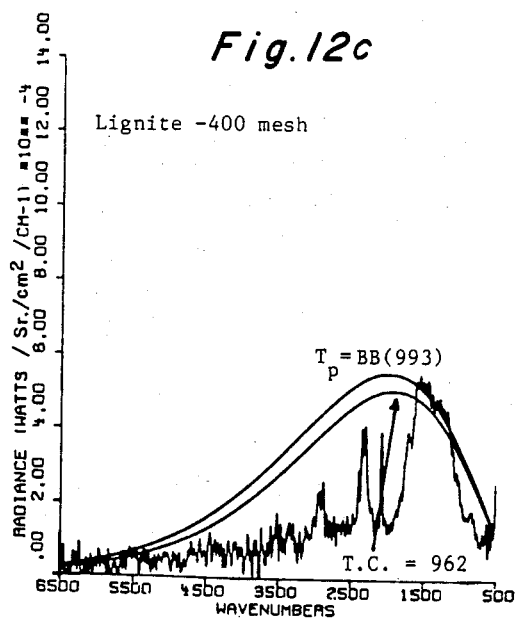
Figure 12D:
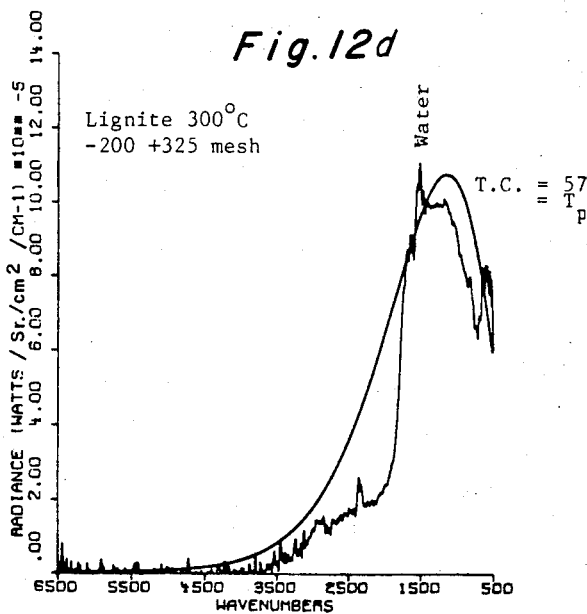
Figure 13A:
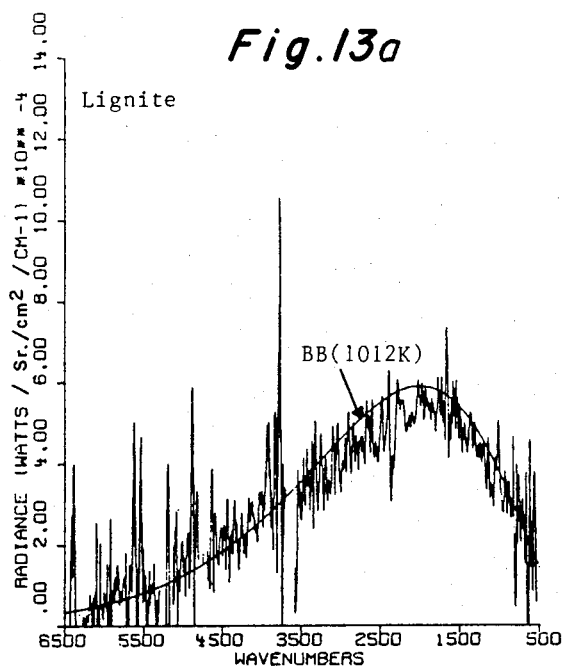
Figure 13C:
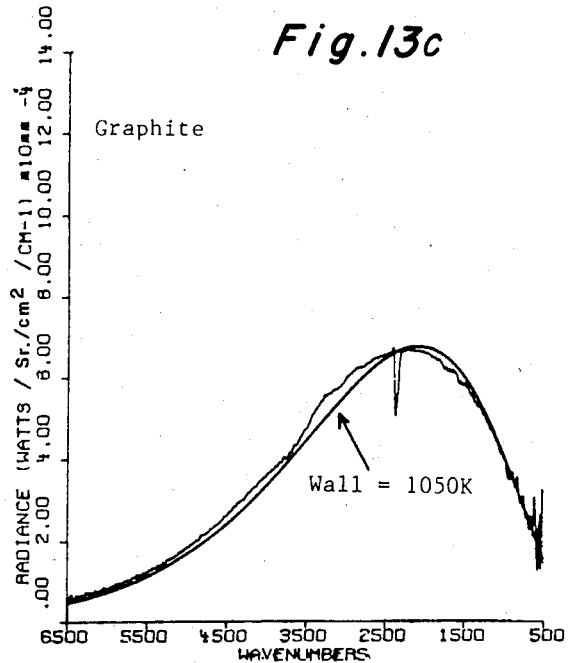
Figure 13B:
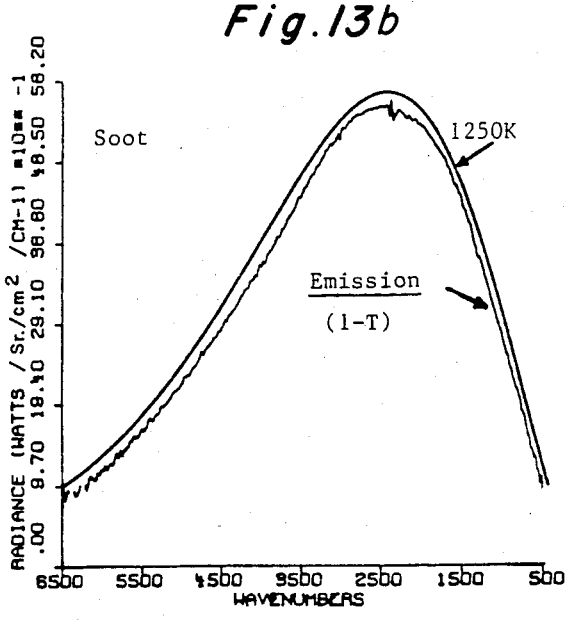
Figure 13D:
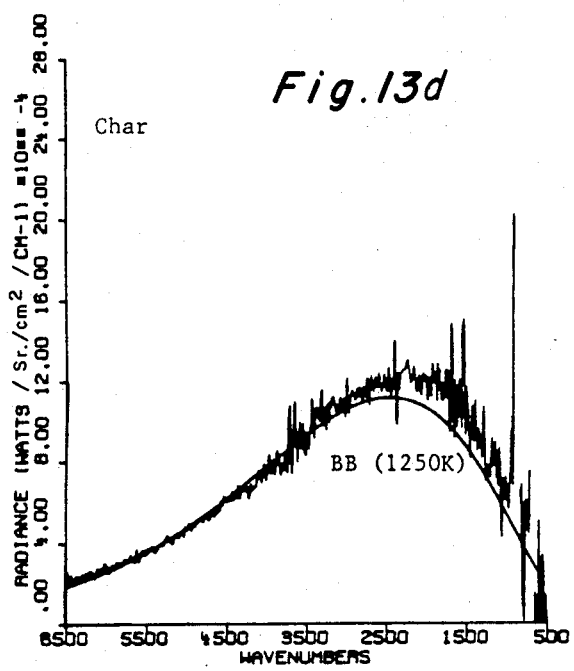
Figure 14A:
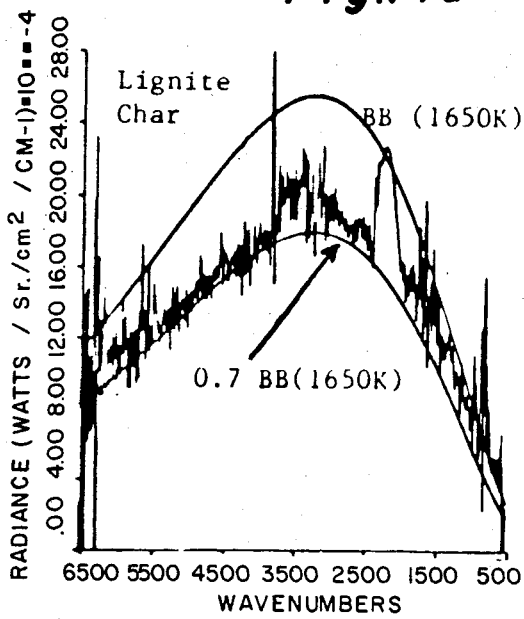
Figure 14C:
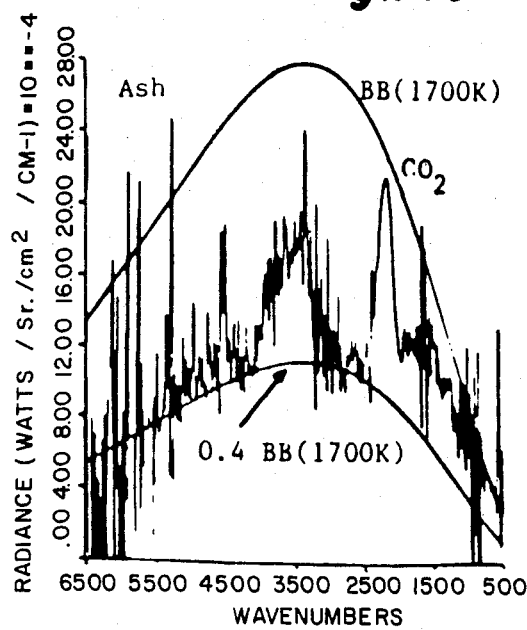
Figure 14B:
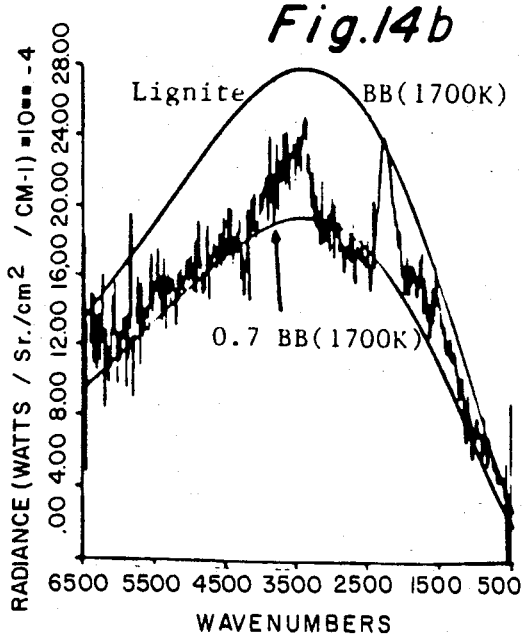
Figure 14D:
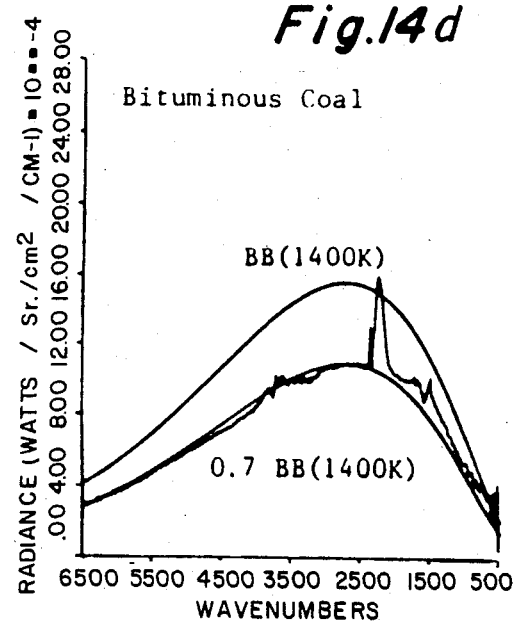

To obtain the emittance of cold particles, the simplest case is for large particles, where $T_w$ is much higher than $T_p$, once again in the absence of soot and absorbing gases, in which case the emittance will be equal to $(1-[E_n/BB(T_w)])$. To determine $\epsilon$, measurements are made in the cell with the wall heated to above 500° Centigrade, and with the particle injector cooled to room temperature or below. Examples of $E_n$ and $BB(T_w)$ for a lignite, potassium chloride, jet fuel and graphite are presented in FIGS. 11a-d. As can be seen, the spectral emittance varies with the sample composition: for potassium chloride it is approximately zero; for graphite, it is almost 80 percent in agreement with expectations; for the lignite (FIG. 11d), the emittance is similar to that determined from the hot lignite (FIG. 12d).

Analysis of Temperature

Temperatures can be obtained for the components of the sample stream even when different components (gas, soot, particles) are not at the same temperature.

a. particle temperature

Considering initially the case in which soot and gas contributions can be neglected ($k_s=k_g=0$), and diffraction effects are small ($Q_{ext}$ is approximately 1), particulate temperature can be determined from black-body curves, through application of the equation: $E_n=\epsilon BB(T_p)+(1-\epsilon) BB(T_w)$. A particularly simple case occurs when the surrounding wall is much colder than the particle, in which case $E_n$ is approximately equal to $BB(T_p)$, and $T_p$ can be determined directly by comparing $E_n$ to computed black-body curves, as in FIGS. 12a–d and 14a–d; $E_n$ falls on the black-body curve in regions where $\epsilon=1$. Another simple case occurs when the particle and wall are in equlibrium, in which case $E_n=BB(T_p)$, as shown in FIGS. 13a–d.

For other cases, the equation expressing $E_n$ in terms of the black-body curve for the wall, provided above, must be solved using an iterative fitting procedure. This requires knowing $\epsilon$ for at least two wavelengths.

b. particle distributions

One difficulty with a shape-based determination of temperature is that a distribution of particle temperatures can give an emission spectrum which appears to be a good black-body shape corresponding to an intermediate temperature. The amplitude, however, is always found to be lower than that of an isothermal distribution at that intermediate temperature, as illustrated in FIGS. 18a,b.

Figure 18A:
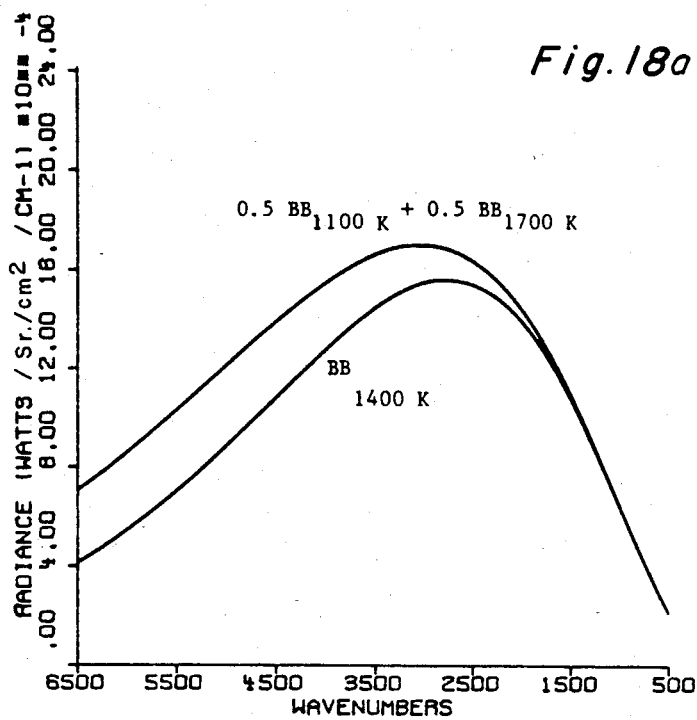
Figure 18B:
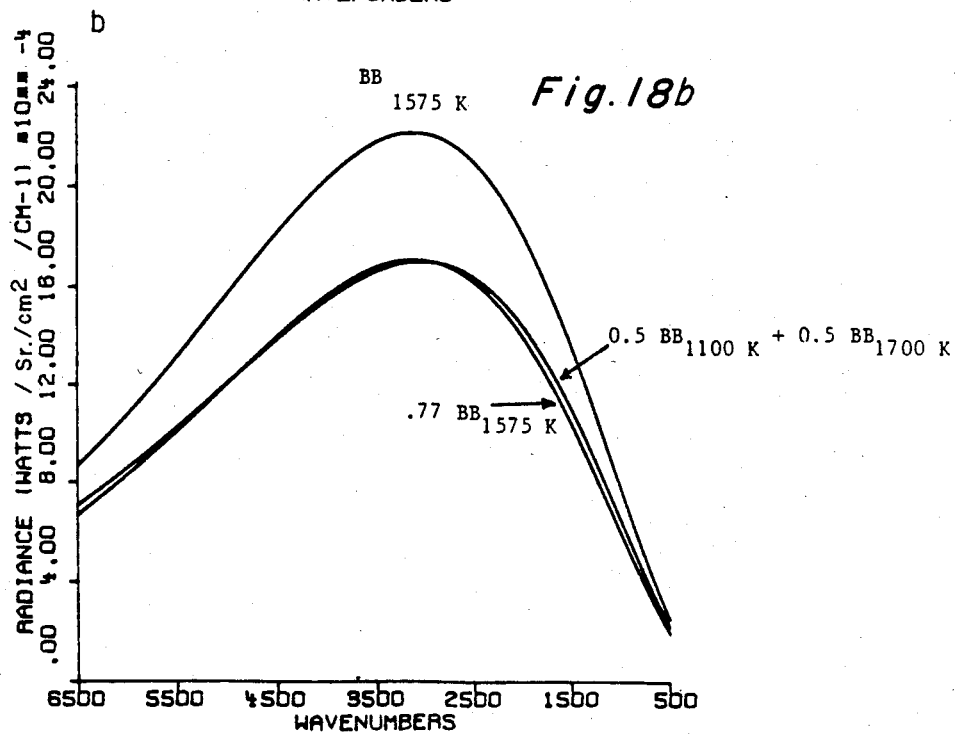

FIG. 18a compares the spectrum for a 50/50 mix of radiators at 1100 and 1700 Kelvin, with an isothermal case at 1400 K (the "average" temperature); there is clearly a difference. The shape of the 50/50 mix curve however can be matched to 0.77 times the black-body curve at 1575 K, as shown in FIG. 18b; therefore, the amplitude of the 50/50 mix does not match the full 1575 black-body curve, and it has been found that the larger the temperature spread, the larger the discrepancy. This illustrates the importance of normalized emission in the particle case. With a good knowledge of $\epsilon$, quantitative information about the average temperature of the particles, and the temperature spread, can be inferred by comparing normalized emission shape and amplitude to black-body curves.

Although normalized emission spectra are obtained only in instances in which transmission can be measured, a similar measurement can be made for emission from an optically thick combusting sample. In that case, a calibration can be made on a sample of known single temperature which fills the spectrometer aperture, and amplitudes would again have significance.

c. temperatures of components in mixed phase systems

In monitoring the properties of reacting mixed phase systems, it is desirable to obtain the temperature of individual phases. For example, in coal combustion the spectra contain continuum contributions from both soot and particulates, as well as band contributions from the gases. To determine relative contributions of each phase to absorbance, and the particle, soot and gas phase temperatures, the last two values are assumed to be the same, and the contribution of $BB(T_w)$ is ignored in the interpretation of the spectra (as will be clear from the context, the subscripts "s", "p", and "g" refer to soot, the particles, and the gas, respectively).

The temperature determinations from the continuum region are made at the three wavenumber regions, chosen because they lie outside of gas emission lines. For $\lambda$ less that five micrometers, $Q_{ext}$ is expected to be unity for particles of diameter greater than about 16 micrometers (see FIG. 16); $Q_{ext}$ is taken to be unity for this analysis. In addition, it is assumed that the values of $\epsilon$ are constant with time, and the appropriate value of $\epsilon$ will be substituted in the generalized equation for "E" set forth above, at the three wavelength regions of interest. From the measured emission and transmission spectra, $-\ln\tau$ and $E_n$ are calculated.

Figure 20A:
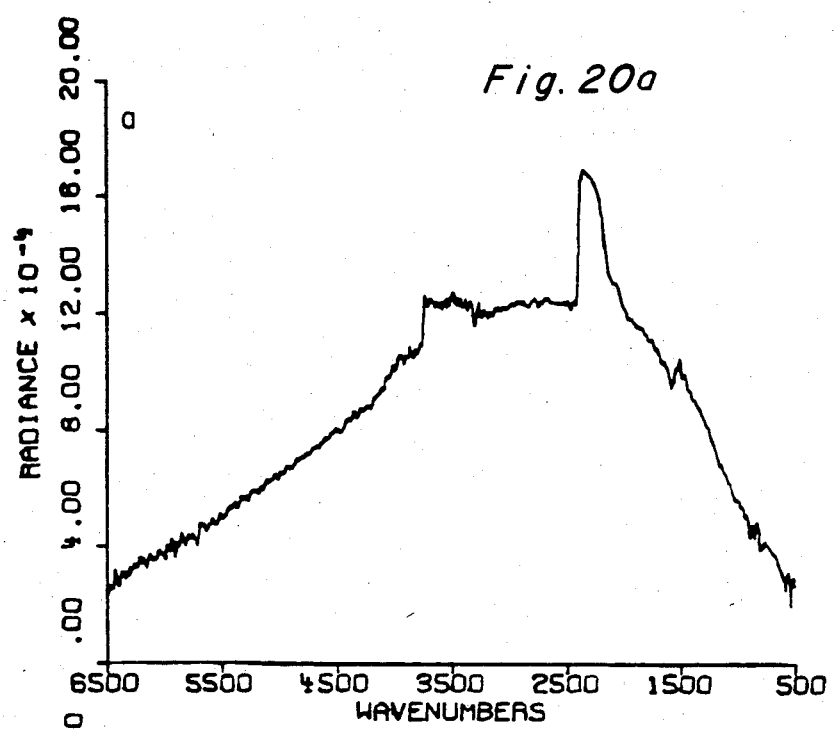
Figure 20B:
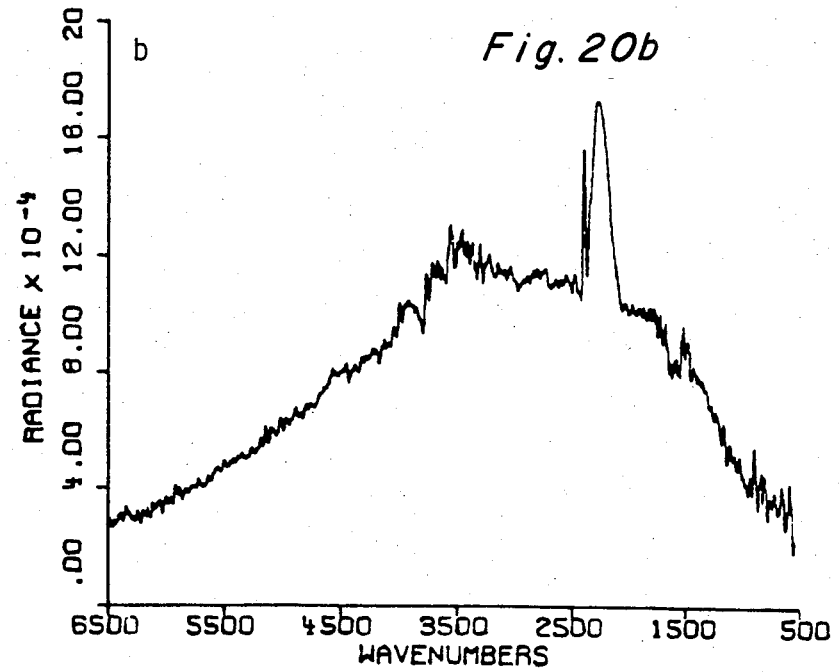

With the above approximations, $-\ln\tau$ (i.e., $(k_s+NA)L$) at the three wavenumber regions of interest is made up of a part that is linear as a function of wavenumber ($k_s$), and a part that is independent (NA). These two straight line contributions can be separated from the $\ln\tau$ data, giving the relative "amounts" of $k_s$ and NA at each wavenumber region, as illustrated in FIGS. 20a,b.

With the approximations made, the normalized emission in the regions free of gas contributions is: $E_n=[k_s BB(T_s)+NA\, BB(T_p)]/(k_s+NA)$, the ratio $k_s$/NA being known from the transmittance, as discussed above. By dividing the above equation by $k_s$ and simplifying, the expression becomes:

$$[E_n(1+NA/k_s)=BB(T_s)+(NA/k_s)\epsilon BB(T_p)]_i$$

the "i" denoting that the equation is for three (or more) wavenumber regions. The unknown quantities are the black-body amplitudes, which can be found by a least squares minimization using an iterative fitting routine, after postulating trial values of $T_s$ and $T_p$. The amplitudes of the black-body curves for all temperatures can be calculated from the black-body reference spectrum.

Figure 19:
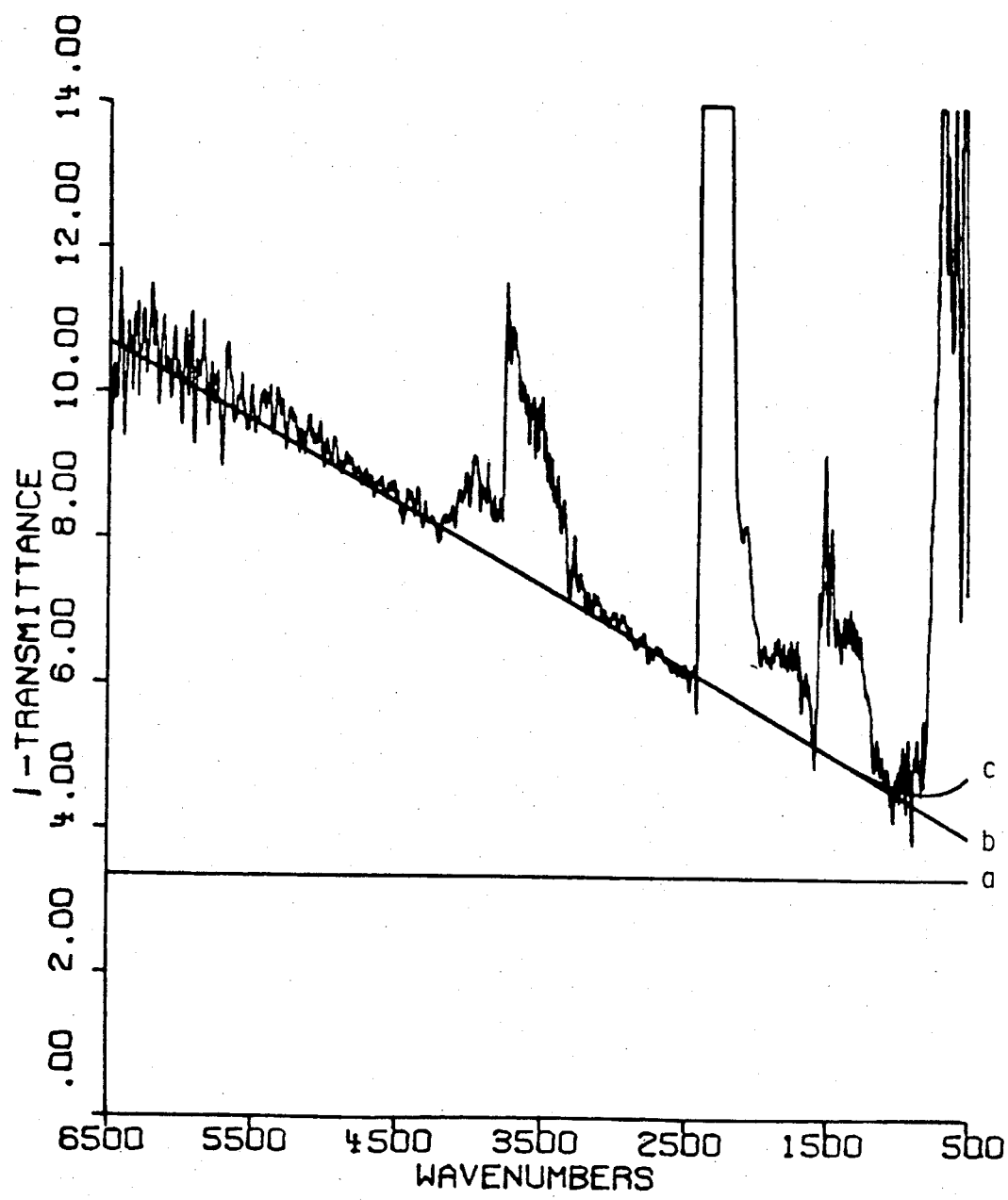

In the region of the spectra containing gas lines, the ratio of $k_g$ to ($k_s+NA$) can be determined from the $-\ln\tau$ curve. With this information, and with known $T_p$ (from the continuum-only measurement discussed above), the gas temperature can be determined from the normalized emission, using the generalized formulas, and the $E_n$ relationship to emission and trasmittance spectra, previously set forth.

Where soot is present, the comparison of $T_s$ and $T_g$ from these two methods will provide an extra check on the data. A comparison of determined $E_n$, with a theoretical $E_n$ made up of separate contributions from gas, soot and particles, is shown in FIGS. 20a and b. The agreement with reasonable values for the temperatures of the separate phases, determined in FIG. 19, is seen to be excellent.

d. particle temperatures from emission only

In obtaining particle temperatures, the use of normalized emission has two advantages: (1) the fit of amplitude, as well as of shape, affords improved precision and the potential for determination of particle temperature spreads; (2) it provides the ability to determine soot temperatures. However, some monitoring applications may preclude the determination of transmittance, which generally requires entrance and exit ports along a line-of-sight, and (extinction-path length) products sufficiently small so that at least 15 percent transmission is achieved. When there is a very small degree of transmission because of particle blocking, the spectra will tend to that of $\epsilon$. For cases without fine soot, a temperature measurement may be obtained from the shape of the ray emission; again, knowledge of $\epsilon$ is required to make this determination more accurate.

For several spectra, a temperature of combusting coal particles has been derived from an "n-color" black-body fit of the raw emission. The n- original colors are the five wavelength regions designated on the raw emission spectra shown in FIGS. 8a–d where interference from gas emission is minimized.

On applying this method to the spectra of combusting species with higher gaseous emission, however, it became clear that only the three higher wavenumber regions could be considered to lie outside of overlapping gas lines. Char is presented in FIG. 8a, lignite in FIG. 8b, and bituminous coal in FIGS. 8c and d; the circled regions of the spectra correspond to the five wavelength regions chosen. Only the three higher wavenumber regions were used for the black-body fits, since the two lower ones appeared to have interference at high water levels.

The measurement is seen to agree well with those from the normalized emission technique, illustrated in FIG. 14a–d. Eliminating the requirements for transmission measurements will make the instant technique more flexible, and therefore more desirable in some situations.

Theory

The scattering, absorption, transmission and emission of electromagnetic radiation by and from particles depend both upon material properties, in the form of optical constants, and on morphology, which can be represented by scales of inhomogeneity relative to wavelength. The interaction of particles with a radiation field can be characterized by wavenumber-dependent efficiency factors "Q", which express the effective cross sections for scattering or absorption, divided by the geometric cross section of the particles; thus $Q_{ext} = Q_s + Q_{abs}$, where the subscripts stand for extinction, scattering and absorption, respectively. As used herein "$Q_s$" refers to radiation scattered out of the acceptance angle of the optics, and the other Q's are similarly specific to the optical beam path.

In developing the basic equation and generalized formulas underlying the analytical techniques and apparatus of this invention, and from which the simplified equations employed for the several analyses are derived, a model was developed to quantitatively account for many features of the observed normalized emission spectra. One feature of the model relates to the geometry of the particles in the sample cell (as described above in connection with FIG. 3), from which it is concluded that the efficiency for scattering of radiation out of the beam path in a transmission experiment (e.g., ray "c") is equal to the efficiency for scattering wall radiation into the beam in an emission experiment (e.g., ray "b"), for particles within the focus volume.

To describe the emission, transmission, and scattering behavior of a multi-phase suspension (i.e., containing gas, particles and soot), the model developed was based upon the assumption that: (1) gas and fine particulates (soot) are at one temperature within the analyzed volume; (2) particles larger than 0.3 micron are at one temperature, not necessarily that of the gas; (3) the molecular concentration of each constituent, averaged over a volume containing many particles, is constant throughout the analyzed volume; and (4) the density of large particles is small, so that less than 0.2 of the radiation is blocked by them. Also, assuming that "L" is the effective path length through a sample located in a cell or reactor, with walls at temperature $T_w$ surrounding the sample volume, the following expressions for the radiation "E" emanating from the cell, and for the radiation (expressed in terms of transmittance "$\tau$") transmitted through the sample, respectively, were developed:

$$E = \frac{[k_s BB(T_s) + k_g BB(T_g) + NA\epsilon BB(T_p) + NAQ_s BB(T_w)][1 - \exp(-(k_s + k_g + NAQ_{ext})L)]}{k_s + k_g + NAQ_{ext}}$$

and $$(1-\tau) = 1 - \exp[-(k_s + k_g + NAQ_{ext})L],$$

the terms of which formulas are defined elsewhere herein. The analysis is readily extended, by use of the above-defined basic equation, or equations derived therefrom, to include ash, to include samples that are non-homogeneous along the path length "L", and to accommodate other deviations from the assumptions made and expressed herein; such analyses will of course be correspondingly more complex.

As noted above, the normalized emission has previously been used for both gaseous and soot flames, in which cases $E_n$ is simply the black-body curve appropriate to the temperature of the flame in both shape and amplitude. The present invention, however, involves the discovery of the significance of normalized emission for particle spectra, and the use thereof for analysis of the several parameters of the particle suspensions discussed herein. It involves, moreover, the discovery of techniques for utilizing the components of spectrum of $ln\tau = (k_s + k_g + NA Q_{ext})L$, the use of $E_n$ to obtain composition data for the particles, and of $\tau$ to obtain particle size and density. Furthermore, it has been found that, in those cases in which $Q_{ext} = 1$, the spectral variation of $\epsilon$ can be determined using normalized emission, together with a measurement of $T_p$ by an auxilliary technique; no other method is believed to exist for determining the spectral emittance of particles.

As discussed above, composition analysis is performed under conditions where the particles are cool and the wall is hot, and in the absence of absorbing gas or soot; where $Q_{ext} = 1$, the normalized emission is approximately equal to the expression: $(1-Q_{abs})BB(T_w)$. The compositional information is contained in the $Q_{abs}$ term, which must be calculated from the properties of the particles.

Mie theory predicts the scattering of radiation of particles as a function of wavelength, particle size, and optical constants. Certain aspects of the present invention utilize the fact that radiation from hot cell walls (or other surrounding medium at a temperature above that of the particles) passes through particles in the center and is diverted along other paths. By collecting the portion of such radiation that is directed towards an emission detector, the detected spectrum, missing energy at wavelengths in the absorption bands of the particle it has passed through, can be used for analysis of composition.

Figure 4:
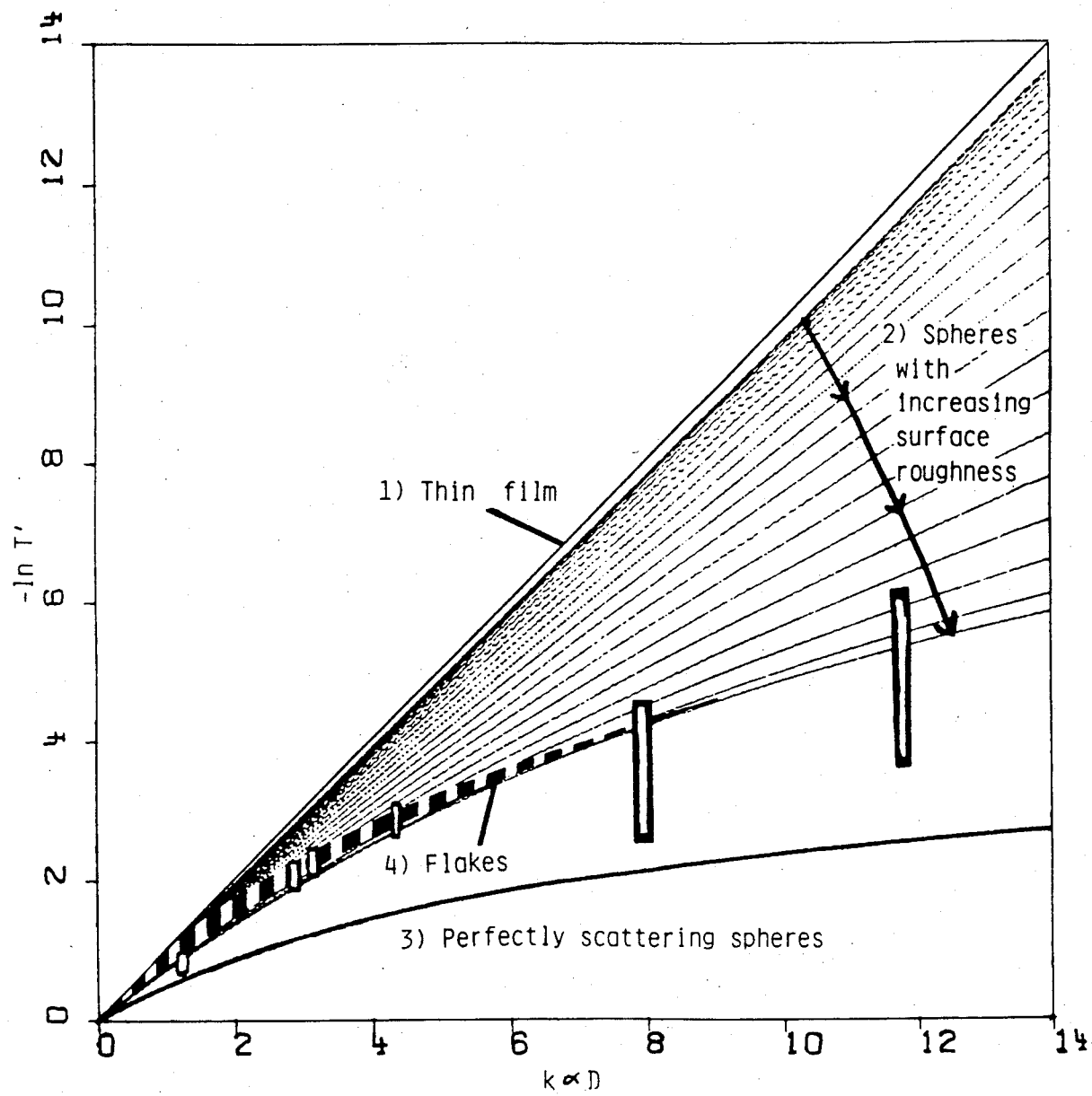
FIGS. 4, 5a and b, 6a–d, 7a–d, 8a–d, 9a–d, 10a–d, 11a–d, 12a–d, 13a–d, 14a–d, 15, 16, 17a and b, 18a and b, 19, and 20a and b are curves of data representative of various relationships significant to the invention.

To optimize this determination, however, it is necessary to predict, based upon the shape and optical constants of the particles, the relative magnitudes of $Q_s$ and $Q_{abs}$; this is done, in accordance herewith, by evaluating effective transmission "T'" of radiation scattered therethrough. The plot of FIG. 4 shows calculations of T' for particles that can be categorized as having one of four basic configurations, or gross geometries; in the plot, "$k_\alpha$" is the wavelength-dependent absorption coefficient, and D is a characteristic dimension for the geometry.

More particularly, a thin film of thickness D will transmit radiation in accordance with Beer's Law, and consequently the expression: $-\ln(T') = k_\alpha D$ will apply; for such particles, $k_d$ will equal $[-\ln(E_n/BB(T_w))/D]$. For sperical particles having a range of surface roughnesses, the effective transmission is given by the equation:

$$T = \sum_d P_{(d)} e^{-k_\alpha d} / \sum_d P_{(d)},$$

wherein the factor "$P_{(d)}$" expresses the probability that any particular ray will travel a distance "d" before emerging from the particle. For perfectly scattering sperical particles, the applicable equation is:

$$T = [1 - e^{-k_\alpha D} / k_\alpha D],$$

wherein D is the particle diameter.

To derive an expression for prismatic flakes (such as coal particles), "D" was taken as the diameter of a sphere of the same volume as the flake, knowing the mesh size and the typical geometry of the sample. In FIG. 4, data bars are extracted from normalized emission spectra of cold coal particles within a hot environment; regions within the $E_n$ spectra for both 170×200 mesh Zap lignite and 400×500 mesh Zap lignite were selected for calculation of these data points. The quantity $(-\ln T')$ is calculated to be $[-\ln(E_n/BB(T_w))]$, corrected to account for a reflective component of five to ten percent. For the chosen regions of the spectra, $k_d$ was determined from potassium bromide pellet spectra. The calculated values of $-\ln T'$ were found to be in good agreement with the measured values.

Thus it can be seen that the present invention provides a novel method, and novel apparatus for carrying it out, by which gaseous suspensions of liquid and/or solid particles can readily be analyzed for any of a variety of physical and chemical properties. The invention provides, more specifically, such a method and apparatus by which a gaseous suspension can be analyzed either in-situ, in a reactive environment, or as a supplied sample, for determinations of particle size, temperature, number density, spectral emittance and/or composition, and which is carried out in a manner that is relatively accurate and is very fast and convenient.

Having thus described the invention, what is claimed is:

1. In apparatus for the analysis of a gaseous suspension of liquid particles, solid particles, or both, the combination comprising:
   (a) interferometer means operatively positionable with respect to the suspension for encoding radiation projected thereinto and radiation emanating therefrom;
   (b) means operatively positionable with respect to the suspension and said interferometer means for collecting coded radiation from the suspension, said collecting means being adapted to discriminate radiation transmitted through the suspension from radiation emanating therefrom, such emanating radiation including any radiation scattered by the particles;
   (c) source means for providing an electromagnetic radiation beam and for projecting it through said interferometer means for coding thereby and for transmission through the suspension; and
   (d) electronic data processing means for analyzing the radiation collected by said collecting means.

2. The apparatus of claim 1 wherein said collecting means comprises a first collector operatively positionable for collecting radiation transmitted through the suspension, and a second collector, separate from said first collector, operatively positionable for collecting radiation emanating therefrom.

3. The apparatus of claim 2 adapted for use with containment means which has a sidewall defining a chamber for the containment of the gaseous suspension to be analyzed, the sidewall in turn having at least one port providing optical access into the chamber thereof, said second collector, and at least one of said source means and said first collector, being disposed on said apparatus for positioning with respect to the one port so as to function therethrough.

4. The apparatus of claim 3 additionally including means defining an aperture of variable size from which passes the transmitted radiation collected by said first collector, so as to improve the capability of said apparatus for making determinations of the size of the particles of the suspension.

5. The apparatus of claim 3 adapted for use with such containment means having a pair of optical access ports aligned transversely on opposite sides of the sidewall thereof, said source means and said first collector being in effective optical alignment with and spaced from one another to accommodate the containment means therebetween, so as to permit projection of the beam from said source means through the aligned access ports to said first collector.

6. The apparatus of claim 3 additionally including a cell cooperatively providing such containment means as an integral component of said apparatus, and means for providing a substantially homogeneous gaseous suspension thereto.

7. The apparatus of claim 6 wherein said cell has a generally cylindrical sidewall and end walls cooperatively defining said chamber thereof, said sidewall having a pair of access ports positioned diametrically thereon, and said end walls having means defining inlet and outlet channels therethrough, aligned substantially on the longitudinal axis of said cell, for the injection and removal of particles thereinto and therefrom, respectively, said means for providing the suspension including said inlet channel, said cell also having means by which the temperature of the inside surface of said sidewall, and the temperature of said inlet and outlet channel defining means, can be independently controlled.

8. The apparatus of claim 7 wherein said inlet channel is adapted to inject said particles as a monodispersed stream.

9. The apparatus of claim 2 wherein said second collector is effectively disposed along the path of radiation between said source means and said interferometer, and wherein said apparatus additionally includes diverter means disposed for establishing a radiation path between the suspension and either said source means, said second collector, or both.

10. The apparatus of claim 9 wherein said diverter means is operative to either permit passage of radiation from said source means to the suspension, or to block such passage of radiation while simultaneously directing radiation from the suspension to said second collecting means, so that measurements of radiation transmitted through and emanating from the suspension, respectively, can be selectively made.

11. The apparatus of claim 9 wherein said diverter means is adapted to simultaneously permit passage of radiation from said source means to the suspension while directing radiation therefrom to said second collecting means, said diverter means having a first portion which is transparent to the radiation from said source means and a second portion which is opaque thereto and is reflective of radiation emanating from the suspension and directed theretoward, so that such transmitted and emanating radiation can simultaneously be measured using said first and second collecting means, respectively.

12. The apparatus of claim 1 comprising a Fourier-transform spectrometer, wherein said spectrometer is adapted to develop a spectrum representative of the intensity of the collected radiation as a function of wavenumber, and wherein said data processing means thereof is programmed to compare the representative spectrum to preestablished spectra indicative of a parameter for which the gaseous suspension is being analyzed, so as to fit the representative spectrum thereto and thus determine the parameter.

13. The apparatus of claim 12 wherein said source means provides radiation of wavelengths in the infrared region, and wherein said data processing means is programmed to effect said comparison by application of at least one of the following basic equation, generalized formulae, and equations derived therefrom:

$$E = \int_0^L [\{k_s BB(T_s) + k_g BB(T_g) + NA\epsilon BB(T_p) + NAQ_s BB(T_w)\} \exp(-y)] dl,$$

wherein "y" is the integral:

$$\int_0^l (k_g + k_s + NAQ_{ext}) dl',$$

$$E = \frac{[k_s BB(T_s) + k_g BB(T_g) + NA\epsilon BB(T_p) + NAQ_s BB(T_w)][1 - \exp(-(k_s + k_g + NAQ_{ext})L)]}{k_s + k_g + NAQ_{ext}}$$

and $$(1-\tau) = 1 - \exp[-(k_s + k_g + NAQ_{ext})L];$$

wherein:

E - represents any collected radiation emanating from the gaseous suspension and not transmitted therethrough, $\tau$ - represents the ratio of any collected radiation that is transmitted through the suspension, divided by radiation that would be transmitted in the absence thereof, $k_s$ and $k_g$ - are the extinction coefficients for any soot present and the gas phases, respectively, of the suspension, $BB(T_s)$, $BB(T_g)$, $BB(T_p)$, and $BB(T_w)$ - are the blackbody spectra appropriate to the temperature of any soot present, the gas, the particles, and the medium surrounding the suspension, respectively, N - is the number density of the particles in the suspension, A - is the geometric cross-sectional area of the particles, L - is the effective path length through the gaseous suspension, and dl is the width of a theoretical slice at position 1 therealong, $\epsilon$ - is the spectral emittance of the particles, $Q_s$ - is the ratio of the radiation scattering cross section to the geometric cross section of the particles, and $Q_{ext}$ - is the ratio of the extinction cross section to the geometric cross section of the particles, and is equal to $Q_s + Q_{abs}$, $Q_{abs}$ being the ratio of the absorption cross section to the geometric cross section of the particles, and wherein the foregoing quantities, other than N, A and L, are wavenumber dependent.

14. In apparatus for the analysis of a gaseous suspension of liquid particles, solid particles, or both, utilizing refracted components of radiation, the combination comprising:

(a) containment means having a sidewall defining a chamber for the flow of a gaseous suspension of particles along a path therethrough, at least one port being provided in said sidewall to provide optical access to said path;

(b) source means for providing electromagnetic radiation directed inwardly from substantially all peripheral points about said path; and (c) means for collecting radiation emanating from said containment means, said containment means, source means and collecting means being so adapted that components of radiation emanating from said source means that have been diverted from their original paths due to interaction with the particles of the suspension can be substantially discriminated from radiation that has not been so diverted.

15. The apparatus of claim 14 additionally including second source means for providing an electromagnetic radiation beam, and second radiation collecting means, said second source means and second collecting means being disposed in effective optical alignment with one another and being adapted to measure radiation transmitted by the particles of the suspension during passage through said containment means.

16. The apparatus of claim 15 additionally including electronic data processing means for analyzing the radiation collected by said first and second collecting means.

17. The apparatus of claim 16 comprising a Fourier-transform spectrometer.

18. The apparatus of claim 16 comprising a Fourier-transform infrared spectrometer, wherein said data processing means thereof is programmed to compare the representative spectrum to preestablished spectra indicative of a parameter for which the gaseous suspension is being analyzed, so as to fit the representative spectrum thereto and thereby determine the parameter, by application of at least one of the following basic equation, generalized formulae, and equations derived therefrom:

$$E = \int_0^L [\{k_s BB(T_s) + k_g BB(T_g) + NA\epsilon BB(T_p) + NAQ_s BB(T_w)\} \exp(-y)] dl,$$

wherein "y" is the integral:

$$\int_0^1 (k_g + k_s + NAQ_{ext}) dl',$$

$$E = \frac{[k_s BB(T_s) + k_g BB(T_g) + NA\epsilon BB(T_p) + NAQ_s BB(T_w)][1 - \exp(-(k_s + k_g + NAQ_{ext})L)]}{k_s + k_g + NAQ_{ext}}$$

and $$(1-\tau) = 1 - \exp[-(k_s + k_g + NAQ_{ext})L];$$

wherein:
- E - represents any collected radiation emanating from the gaseous suspension and not transmitted therethrough,
- $\tau$ - represents the ratio of any collected radiation that is transmitted through the suspension, divided by radiation that would be transmitted in the absence thereof,
- $k_s$ and $k_g$ - are the extinction coefficients for any soot present and the gas phase, respectively, of the suspension,
- $BB(T_s)$, $BB(T_g)$, $BB(T_p)$, and $BB(T_w)$ - are the blackbody spectra appropriate to the temperature of any soot present, the gas, the particles, and the medium surrounding the suspension, respectively,
- N - is the number density of the particles in the suspension,
- A - is the geometric cross-sectional area of the particles,
- L is the effective path length through the gaseous suspension, and dl is the width of a theoretical slice at position 1 therealong,
- $\epsilon$ - is the spectral emittance of the particles,
- $Q_s$ - is the ratio of the radiation scattering cross section to the geometric cross section of the particles, and
- $Q_{ext}$ - is the ratio of the extinction cross section to the geometric cross section of said particles, and is equal to $Q_s + Q_{abs}$, $Q_{abs}$ being the ratio of the absorption cross section to the geometric cross section of the particles, and wherein the foregoing quantities, other than N, A and L, are wavenumber dependent.

19. The apparatus of claim 15 wherein said sidewall of said containment means has a second optical access port therein aligned transversely with said one port on the opposite side of said flow path, said second source means and second collecting means being effectively disposed to opposite sides of said containment means and optically aligned with one another through said access ports.

20. The apparatus of claim 14 wherein said sidewall of said containment means substantially surrounds said flow path and has an energy radiating surface thereon providing said first-mentioned source means, the configuration of said sidewall surface and the positions thereof and of said collecting means with respect to said access port substantially limiting the radiation from said surface impinging upon said collecting means to that which has been so diverted, so as to effectively provide the radiation discrimination capability of said apparatus.

21. The apparatus of claim 20 wherein said radiating surface is of generally circular cross-sectional configuration in planes transverse to the flow path axis.

22. The apparatus of claim 21 wherein said sidewall of said containment means has a second optical access port therein aligned transversely with said one port on the opposite side of said flow path, said second port providing a non-radiating area on said surface and thereby cooperating to provide the discrimination capability of said apparatus.

23. The apparatus of claim 20 wherein said containment means includes means for heating said energy radiating surface.

24. The apparatus of claim 23 having a sample compartment adapted for seating a cell, and additionally including a cell seated within said sample compartment and providing containment means for said apparatus.

25. The apparatus of claim 15 additionally including means for coding the radiation from said second source means, said second collecting means being adapted to discriminate the coded radiation from other radiation which may impinge thereupon.

26. The apparatus of claim 25 wherein said coding means comprises an interferometer effectively interposed in the path of radiation from said second source means to said containment means.

27. The apparatus of claim 26 wherein said first-mentioned collecting means is disposed along said path of radiation, effectively between said second source means and said interferometer, and wherein said system additionally includes diverter means for establishing a radiation path between said containment means and either said second source means, said first collecting means, or both, so that measurements of radiation transmitted through and/or emanating from said containment means can be made, respectively.

28. The apparatus of claim 27 wherein said diverter means is operative to selectively either permit passage of radiation from said second source means to said containment means, or block such passage of radiation while simultaneously directing radiation from said containment means to said first collecting means.

29. The apparatus of claim 27 wherein said diverter means is adapted to simultaneously permit passage of radiation from said second source means to said containment means while directing radiation therefrom to said first collecting means, said diverter means having a first portion which is transparent to the radiation from said second source means, and a second portion which is opaque thereto and is reflective of radiation from said containment means and directed theretoward, so that such transmitted and emanating radiation can simultaneously be measured using said second and first collecting means, respectively.

30. The apparatus of claim 24 wherein said cell has a generally cylindrical sidewall and end walls cooperatively defining said chamber thereof, said sidewall having a pair of access ports positioned diametrically thereon, and said end walls having means defining inlet and outlet channels therethrough, aligned substantially on the longitudinal axis of said cell, for the injection and removal of particles thereinto and therefrom, respectively, said inlet channel providing means for injecting the suspension, said cell also having means by which the temperature of said inlet and outlet channel defining means can be controlled independently of said means for heating said radiating surface.

31. In a method for the analysis of at least one parameter of a gaseous suspension of liquid or solid particles, or both, the steps comprising:

a. providing a gaseous suspension of particles;
 b. causing electromagnetic radiation from at least one source to impinge upon said suspension;
 c. collecting spectral radiation from said so irradiated suspension;
 d. developing a spectrum representative of the intensity of the collected radiation as a function of wavenumber; and
 e. comparing said representative spectrum to preestablished spectra indicative of the parameter for which said suspension is being analyzed, and fitting said representative spectrum thereto to determine said parameter, said comparison being made by application of the basic equation, or equations derived therefrom:

$$E = \int_0^L [\{k_s BB(T_s) + k_g BB(T_g) + NA\epsilon BB(T_p) + NAQ_s BB(T_w)\} \exp(-y)] dl,$$

wherein "y" is the integral:

$$\int_0^1 (k_g + k_s + NAQ_{ext}) dl',$$

and wherein:

E - represents any collected radiation emanating from said gaseous suspension and not transmitted therethrough, $k_s$ and $k_g$ - are the extinction coefficients for any soot present and the gas phases, respectively, of the suspension, $BB(T_s)$, $BB(T_g)$, $BB(T_p)$, and $BB(T_w)$ - are the blackbody spectra appropriate to the temperature of any soot present, the gas, the particles, and the medium surrounding said suspension, respectively, N - is the number density of the particles in the suspension, A - is the geometric cross-sectional area of said particles, L - is the effective path length through the gaseous suspension, and dl is the width of a theoretical slice at position 1 therealong, $\epsilon$ - is the spectral emmittance of the particles, $Q_s$ - is the ratio of the radiation scattering cross section to the geometric cross section of the particles, and $Q_{ext}$ - is the ratio of the extinction cross section to the geometric cross section of said particles, and is equal to $Q_s + Q_{abs}$, $Q_{abs}$ being the ratio of the absorption cross section to the geometric cross section of the particles, and wherein the foregoing quantities, other than N, A and L, are wavenumber dependent.

32. The method of claim 31 wherein said suspension provided is substantially homogeneous, and wherein said comparison is made by application of at least one of the generalized formulae:

$$E = \frac{[k_s BB(T_s) + k_g BB(T_g) + NA\epsilon BB(T_p) + NAQ_s BB(T_w)][1 - \exp(-(k_s + k_g + NAQ_{ext})L)]}{k_s + k_g + NAQ_{ext}}$$

and $$(1-\tau) = 1 - \exp[-(k_s + k_g + NAQ_{ext})L],$$

wherein "$\tau$" represents the ratio of any collected radiation that is transmitted through the suspension, divided by radiation that would be transmitted in the absence thereof.

33. The method of claim 32 including the step of passing said gaseous suspension to be analyzed through a chamber, having at least one port for optical access thereinto, at a flow rate of about 1 to 100 meters per second, said step "b" being effected during passage of said suspension through said chamber.

34. The method of claim 33 including the additional step of passing a stream of gas into said chamber simultaneously with and as a sheath about said particle suspension.

35. The method of claim 33 wherein said electromagnetic radiation is a beam brought to a focal volume within said chamber, and wherein said suspension of particles is passed substantially through said focal volume.

36. The method of claim 35 wherein said particles in said suspension are in the form of a monodispersed stream.

37. The method of claim 31 wherein electromagnetic radiation of infrared wavelengths is utilized for irradiating said suspension.

38. The method of claim 32 wherein electromagnetic radiation of infrared wavelengths is utilized for irradiating said suspension, and wherein the analysis of said radiation comprises Fourier-transform spectroscopic measurement thereof.

39. In a method for the analysis of at least one parameter of a gaseous suspension of liquid or solid particles, or both, the steps comprising:

a. causing a beam of electromagnetic radiation to impinge upon the suspension to be analyzed;
 b. collecting radiation transmitted through and emanating from said so irradiated suspension;
 c. distinguishing said transmitted radiation from said emanating radiation;

d. developing spectra representative of the intensity of the transmitted and emanating radiation collected and distinguished in said steps b. and c., as functions of wavenumber; and e. comparing said representative spectra to preestablished spectra indicative of a parameter for which said suspension is being analyzed, and fitting said representative spectra thereto to determine said parameter.

40. The method of claim 39 including the additional step of providing said suspension as a substantially homogeneous volume, and wherein said comparison is made by application of the generalized formulas:

$$E = \frac{[k_s BB(T_s) + k_g BB(T_g) + NA\epsilon BB(T_p) + NAQ_s BB(T_w)][1 - \exp(-(k_s + k_g + NAQ_{ext})L)]}{k_s + k_g + NAQ_{ext}}$$

and $$(1-\tau) = 1 - \exp[-(k_s + k_g + NAQ_{ext})L];$$

wherein:

E - represents any collected radiation emanating from said gaseous suspension and not transmitted therethrough, $\tau$ - represents the ratio of any collected radiation that is transmitted through the suspension, divided by radiation that would be transmitted in the absence thereof, $k_s$ and $k_g$ - are the extinction coefficients for any soot present and the gas phases, respectively, of the suspension, $BB(T_s)$, $BB(T_g)$, $BB(T_p)$, and $BB(T_w)$ - are the blackbody spectra appropriate to the temperature of any soot present, the gas, the particles, and the medium surrounding said suspension, respectively, N - is the number density of the particles in the suspension, A - is the geometric cross-sectional area of said particles, L - is the effective path length through the gaseous suspension, $\epsilon$ - is the spectral emittance of the particles, $Q_s$ - is the ratio of the radiation scattering cross section to the geometric cross section of the particles, and $Q_{ext}$ - is the ratio of the extinction cross section to the geometric cross section of said particles, and is equal to $Q_s + Q_{abs}$, $Q_{abs}$ being the ratio of the absorption cross section to the geometric cross section of the particles, and wherein the foregoing quantities, other than N, A and L, are wavenumber dependent.

41. The method of claim 40 wherein the temperature "$T_w$" of the medium surrounding said suspension is known and said parameter for analysis is particle temperature "$T_p$", said representative spectrum being that of normalized emission "$E_n$", wherein $E_n = E/(1-\tau)$.

42. The method of claim 41 wherein said step "a" is carried out under conditions at which $Q_{ext}$ has a value of 1, at frequencies at which there is no absorption of radiation by soot or the gas phase, or such absorption can be ignored, and with said gaseous suspension to be analyzed contained in a chamber having at least one port for optical access thereinto, said surrounding medium being the wall surface defining said chamber and said comparison being made based upon the equation:

$$E_n = \epsilon BB(T_p) + (1-\epsilon)BB(T_w).$$

43. The method of claim 40 wherein the temperature "$T_p$" of said particles and the temperature "$T_w$" of the medium surrounding said suspension are known, and said parameter for analysis is emittance "$\epsilon$", said representative spectrum being that of normalized emission "$E_n$", wherein $E_n = E/(1-\tau)$.

44. The method of claim 43 wherein said particle temperature "$T_p$" is substantially higher than said surrounding medium wall surface temperature "$T_w$", said comparison being made based upon the equation:

$$\epsilon = E_n/BB(T_p).$$

45. The method of claim 43 wherein said surrounding medium comprises the surface of a wall defining a chamber in which said suspension is contained when said step "a" is carried out, and wherein the temperature "$T_w$" of said wall surface is substantially higher than said particle temperature "$T_p$", said comparison being made based upon the equation:

$$\epsilon = 1 - [E_n/BB(T_w)].$$

46. The method of claim 45 including the further step of estimating the wavenumber-dependent linear absorption coefficient characteristic "$k_\alpha$" of said composition, said estimation being carried out by measuring the value of $E_n$; determining a value for the average transmission "T'" for the inside of the particles of said suspension by application of the equation:

$$T' = E_n/BB(T_w);$$

characterizing the gross geometry of the particles of said suspension in terms of a characterizing dimension "D"; selecting, based upon said characterization of geometry, a suitable preestablished curve expressing $(-\ln T')$ as a function of $k_\alpha D$; and estimating the value of $k_\alpha$ from said selected curve.

47. In a method for the quantitative compositional analysis of a gaseous suspension of liquid or solid particles, or both, the steps comprising:

a. passing a gaseous suspension of particles to be analyzed into a chamber having at least one port for optical access thereinto;

b. causing electromagnetic radiation from at least one source to impinge at off axis angles upon the particles of said suspension during passage through said chamber, said off-axis angles consisting essentially of angles oblique to said one access port;

c. collecting through said one port radiation from said so irradiated particles, said collected radiation being limited, by virtue of said off-axis impingement, substantially to rays from said source refracted or otherwise diverted by said particles;

d. developing a spectrum representative of the path and amplitude of said collected radiation as a function of wavenumber; and e. comparing said representative spectrum to preestablished spectra indicative of the compositional parameter for which said suspension is being analyzed, and fitting said representative spectrum thereto to determine said parameter.

48. The method of claim 47 wherein said chamber is defined by a wall substantially surrounding said gaseous suspension, and wherein the surface of said wall is maintained at a temperature substantially higher than the temperature of said particles and provides said one radiation source.

49. The method of claim 48 wherein said suspension is passed through said chamber at a flow rate sufficiently high to avoid substantial heating of said particles by the radiant energy emanating from said wall surface.

50. The method of claim 49 wherein said wall surface is at a temperature about 500 Kelvin degrees or more above the temperature of said particles.

51. The method of claim 50 wherein, prior to entry into said chamber, said suspension is maintained at a temperature suitable to ensure that said particles thereof will be substantially at room temperature therein.

52. The method of claim 48 wherein said wall surface is of substantially circular cross-section in planes perpendicular to the flow axis of said suspension, and wherein said diverted radiation is collected at a location diametrically disposed with respect to a second optical access port in said wall surface, said second port being on-axis and constituting a non-radiating area of said wall surface, as to so limit said collected radiation.

53. The method of claim 48 wherein a beam of electromagnetic radiation from a second source is caused to impinge upon said particles, said collecting step being carried out by collecting and discriminating said diverted rays from components of said radiation beam transmitted through said particles, said representative spectrum being that of normalized emission "$E_n$", wherein $E_n = E/(1-\tau)$.

54. The method of claim 53 wherein said suspension is substantially homogeneous, and wherein said comparison is made by application of the following generalized formulae:

$$E = \frac{[k_s BB(T_s) + k_g BB(T_g) + NA\epsilon BB(T_p) + NAQ_s BB(T_w)][1 - \exp(-(k_s + k_g + NAQ_{ext})L)]}{k_s + k_g + NAQ_{ext}}$$

and $$(1-\tau) = 1 - exp[-(k_s + k_g + NAQ_{ext})L],$$

wherein:
- E - represents any collected radiation emanating from said gaseous suspension and not transmitted therethrough,
- $\tau$ - represents the ratio of any collected radiation that is transmitted through the suspension, divided by radiation that would be transmitted in the absence thereof,
- $k_s$ and $k_g$ - are the extinction coefficients for any soot present and the gas phases, respectively, of the suspension,
- $BB(T_s)$, $BB(T_g)$, $BB(T_p)$, and $BB(T_w)$ - are the blackbody spectra appropriate to the temperature of any soot present, the gas, the particles, and the medium surrounding said suspension, respectively,
- N - is the number density of the particles in the suspension,
- A - is the geometric cross-sectional area of said particles,
- L - is the effective path length through the gaseous suspension,
- $\epsilon$ - is the spectral emittance of the particles,
- $Q_s$ - is the ratio of the radiation scattering cross section to the geometric cross section of the particles, and
- $Q_{ext}$ - is the ratio of the extinction cross section to the geometric cross section of said particles, and is equal to $Q_s + Q_{abs}$, $Q_{abs}$ being the ratio of the absorption cross section to the geometric cross section of the particles, and wherein the foregoing quantities, other than N, A and L, are wavenumber dependent.

55. The method of claim 54 wherein said transmitted radiation components and said diverted rays are collected sequentially with said suspension flowing at a constant rate through said chamber.

56. The method of claim 54 wherein said transmitted radiation components and said diverted rays are collected simultaneously.

57. The method of claim 54 including the further step of estimating the wavenumber-dependent linear absorbtion coefficient characteristic "$k_\alpha$" of said composition, said estimation being carried out by measuring the value of $E_n$; determining a value for the average transmission "T'" for the inside of the particles of said suspension by application of the equation:

$$T' = E_n/BB(T_w);$$

characterizing the gross geometry of the particles of said suspension in terms of a characterizing dimension "D"; selecting, based upon said characterization of geometry, a suitable preestablished curve expressing $(-\ln T')$ as a function of $k_\alpha D$; and estimating the value of $k_\alpha$ from said selected curve.

58. In a method for the analysis of particle size in a gaseous suspension of liquid or solid particles, or both, the steps comprising:

a. providing a substantially homogeneous gaseous suspension of particles;

b. causing a beam of electromagnetic radiation to impinge upon said suspension;

c. selectively collecting radiation transmitted through said so irradiated suspension;

d. developing a spectrum representative of the intensity of the collected radiation as a function of wavenumber; and e. comparing said representative spectrum to preestablished spectra indicative of particle size, and fitting said representative spectrum thereto to determine a particle size parameter, said representative spectrum being that of $(1-\tau)$ and said comparison being made based upon the formula:

$$(1-\tau) = 1 - exp[-(k_s + k_g + NAQ_{ext})L]$$

wherein:
- $k_s$ and $k_g$ - are the extinction coefficients for any soot present and the gas phase, respectively, of said suspension,
- N - is the number density of said particles in said suspension,
- A - is the geometric cross-sectional area of said particles,
- L - is the effective path length through said gaseous suspension, and $Q_{ext}$ - is the ratio of the extinction cross section to the geometric cross section of said particles, and is equal to $Q_s+Q_{abs}$, $Q_{abs}$ being the ratio of the absorption cross section to the geometric cross section of said particles, and $Q_s$ being the ratio of the radiation scattering cross section to the geometric cross section of said particles, the quantities other than N, A and L being wavenumber dependent.

59. The method of claim 58 wherein said step "b" is carried out with said gaseous suspension to be analyzed contained in a chamber having a pair of aligned ports for optical access thereinto, and wherein the aperture size of the one of said ports lying beyond the zone of interaction of said beam with said particles, relative to the source thereof, is varied so as to maximize the dependency of said collected radiation intensity upon the wavenumbers of radiation of said impinging beam, so as to optimize the curve of said representative spectrum for fitting to curves of said preestablished spectra.

* * * * *

UNITED STATES PATENT AND TRADEMARK OFFICE
CERTIFICATE OF CORRECTION

PATENT NO.  : 4,652,755

DATED       : March 24, 1987

INVENTOR(S) : Solomon et al

It is certified that error appears in the above-identified patent and that said Letters Patent is hereby corrected as shown below:

On the Title Page, "51 Drawings Figures" should read --53 Drawing Figures--

In the drawings, Figures 1b and 1c should be included; they are as appended.

Signed and Sealed this

Twenty-fifth Day of August, 1987

*Attest:*

DONALD J. QUIGG

*Attesting Officer*     *Commissioner of Patents and Trademarks*